United States Patent
Muta et al.

(10) Patent No.: US 7,365,352 B2
(45) Date of Patent: Apr. 29, 2008

(54) GAS CONCENTRATION FLUX MEASURING DEVICE

(75) Inventors: Kenji Muta, Yokohama (JP);
Masazumi Tanoura, Yokohama (JP);
Ko Nakaya, Abiko (JP)

(73) Assignees: Mitsubishi Heavy Industries, Ltd., Tokyo (JP); Central Research Institute of Electric Power Industry, Tokyo (JP)

( * ) Notice: Subject to any disclaimer, the term of this patent is extended or adjusted under 35 U.S.C. 154(b) by 51 days.

(21) Appl. No.: 10/570,344

(22) PCT Filed: Sep. 28, 2004

(86) PCT No.: PCT/JP2004/014159
§ 371 (c)(1),
(2), (4) Date: Mar. 29, 2006

(87) PCT Pub. No.: WO2005/031275
PCT Pub. Date: Apr. 7, 2005

(65) Prior Publication Data
US 2006/0262311 A1    Nov. 23, 2006

(30) Foreign Application Priority Data
Sep. 29, 2003  (JP)  ............................. 2003-338466

(51) Int. Cl.
*G01N 15/06*  (2006.01)
*G01N 21/49*  (2006.01)
*G01N 21/85*  (2006.01)

(52) U.S. Cl. ...................... 250/573; 356/437; 73/24.02

(58) Field of Classification Search ............ 250/341.3, 250/343, 345, 573–575, 339.13; 356/437; 73/24.02, 30.01–30.04, 31.01
See application file for complete search history.

(56) References Cited
U.S. PATENT DOCUMENTS
5,026,991 A * 6/1991 Goldstein et al. ........... 250/343
(Continued)

FOREIGN PATENT DOCUMENTS
JP    8-261891    10/1996
(Continued)

OTHER PUBLICATIONS
Yoshinari Goto, "Characteristics of Turbulent Intensities and Simplified Methods for Estimating Temperture and Specific Humidity Fluxes in the Unstable Stratification", Journal of Japan Society of Hydrology & Water Resources, vol. 13, No. 2, 2000, pp. 114-123 (with partial English translation).
(Continued)

Primary Examiner—Kevin Pyo
Assistant Examiner—Seung C Sohn
(74) Attorney, Agent, or Firm—Wenderoth, Lind & Ponack, L.L.P.

(57) ABSTRACT

A gas flux measuring device measures a region, such as a forest, as a measuring object with no influence by concomitants and with high responsiveness and excellent measuring stability. The device includes a laser beam source, laser output controller, wavelength modulation controller, first light receiver, first direct current component detector, first wavelength modulation demodulator, optical system, reference cell, second light receiver, second direct current component detector, second wavelength modulation demodulator, third wavelength modulation demodulator, analyzer, adder, temperature measurement and pressure measurement. A flow velocity measuring device directly measures horizontal 2-directional flow velocity components and a vertical directional flow velocity component of a gas flow in the measuring region and puts out these measurement signals into the analyzer. Based on the signals inputted from the flow velocity measuring device, the analyzer makes an analysis based on the eddy correlation method and obtains, by calculation using this analysis result, a momentum flux and concentration of the measuring object gas.

21 Claims, 22 Drawing Sheets

U.S. PATENT DOCUMENTS

| | | | |
|---|---|---|---|
| 5,047,639 A * | 9/1991 | Wong | 250/341.1 |
| 5,303,024 A | 4/1994 | Thierman | |
| 6,064,488 A * | 5/2000 | Brand et al. | 356/440 |

FOREIGN PATENT DOCUMENTS

| | | | |
|---|---|---|---|
| JP | 8-261892 | | 10/1996 |
| JP | 9-236542 | | 9/1997 |
| JP | 10-153548 | | 6/1998 |
| JP | 11337483 | A * | 12/1999 |
| JP | 2001-74653 | | 3/2001 |
| JP | 2001074654 | A * | 3/2001 |
| JP | 2004-219379 | | 8/2004 |

OTHER PUBLICATIONS

Volker Thiermann, "A Displaced-Beam Scintillometer for Line-Averaged Measurements of Surface Layer Turbulence", Tenth Symposium on Turbulence and Diffusion, Sep. 19-Oct. 2, 1992, pp. 224-247.

O. Nakaya et al. "Analysis of Turbulence Characteristics for Assessment of $CO_2$ Flux in Birch Forests of the East Foot of Mt. Asama", Lecture at Joint Meeting of Four Academies related to Agricultural Environment Engineering, Aug. 6-8, 2002 at the Faculty of Agriculture, Tokyo, University (with partial English translation).

N. Kagawa et al., "Velocimetry Using Spatial Filtering of Scintillation of Laser Beam", Publication of Electronics, Information and Systems Society, vol. 118-C, No. 12, Dec. 1998, pp. 1792-1797 (with partial English translation).

N. Moji, "Proposal on GHG (green house gas) Flux Measuring Method in Forests", Center for Global Environment Research, National Institute for Environmental Studies, Environment Agency of Japan, 2000, pp. 3-80 (with partial English translation).

Jun Asanuma et al., "Turbulence Variance Characteristics Above a Flat Pine Forest and the Surface Flux Estimation with Variance Methods", Journal of Japan Society of Hydrology & Water Resources, vol. 10, No. 6, 1997, pp. 515-523 (with partial English translation).

O. Nakaya et al., "Introduction of $CO_2$ Flux Continuous Observations in Birch Forests of the East Foot of Mt. Asama", 2002 CGER Flux Research Meeting, Nov. 14, 2002, p. 58 (with partial English translation).

* cited by examiner

Fig. 16B

The followings are obtained by repeated calculations based on the MOS law.

(1) MO length $\quad z/L = kgz(H/Cp\, Ta + 0.61E)/[-u^{*3}\rho]$ (2) Friction velocity $\quad u^* = [kz\, \varepsilon/(\phi_\varepsilon(z/L))]^{1/3}$ (3) Sensible heat flux $\quad H = \rho Cp[kzu^*\, \varepsilon_T/\phi_{\varepsilon T}(z/L)]^{1/2}$ (4) Latent heat flux $\quad LE = \rho L[kzu^*\, \varepsilon_q/\phi_{\varepsilon q}(z/L)]^{1/2}$ $z$ : Measuring height, $k$ : Karman Constant, $g$ : Gravitational acceleration,
$Cp$ : Constant pressure specific heat of air, $\rho$ : Air density
$\phi n(z/L)$ : Monin-Obukhov universal function ($n = \varepsilon,\ \varepsilon_T,\ \varepsilon_q$)

Momentum Flux = $\rho \overline{u'w'}$

Sensible heat flux = $\rho cp \overline{T'w'}$

Water vapor flux = $\rho L \overline{q'w'}$

Fig. 17B (2) Calculation of dissipation rate $\varepsilon_q$ of temperature $$\varepsilon_q = C_q^2 / f_q(\varepsilon)$$

⇒ Analysis based on MOS law

① L: Obukhov length: $\dfrac{z}{L} = \dfrac{k_v \cdot g \cdot z \cdot T_*}{u_*^2 \cdot T}$ ② $u_*$: Friction velocity = $\overline{(-u' \cdot w')}^{1/2} = \dfrac{k_v \cdot z \cdot e}{f_u = (z/L)}$ ③ $T_*$: Friction temperature = $\overline{(w' \cdot T')} = \dfrac{k_v \cdot z \cdot e_T}{f_T = (z/L)}$ ④ $Q_*$: Friction specific humidity = $\overline{(w' \cdot Q')} = \dfrac{k_v \cdot z \cdot e_q}{f_q = (z/L)}$ ⑤ $G_*$: Friction specific concentration = $\overline{(w' \cdot G')} = \dfrac{k_v \cdot z \cdot e_g}{f_g = (z/L)}$ · z: Measuring length
· $k_v$: von Karman Constant
· g: Gravitational constant

⇧

(1) Gas flux: $G = \rho \cdot u_* \cdot G_*$ (2) Momentum flux: $M = \rho \cdot u_*^2$ (3) Sensible heat flux: $H = Cp \cdot \rho \cdot u_* \cdot T_*$ (4) Latent heat flux: $E = L_\theta \cdot \rho \cdot u_* \cdot Q_*$ · $\rho$: Air density
· Cp: Air constant pressure specific heat
· $L_\theta$: Latent heat

GAS CONCENTRATION FLUX MEASURING DEVICE

TECHNICAL FIELD

The present invention relates to a gas flux measuring device used for such purposes as an assessment of $CO_2$ absorption quantity by a forest, an investigation of the environment, such as an investigation of generation quantity of greenhouse gases (GHG) coming out of the ground, and a detection of gas leakage such as $CO_2$ from underground disposal plants, gas storage facilities, pipelines, etc.

BACKGROUND ART

Recently, keen attention is being paid to the problem of global warming due to GHG, such as $CO_2$, $CH_4$, $N_2O$ or the like. To determine a discharge/leakage quantity of various GHG from the ground or industrial plants or to determine a $CO_2$ absorption quantity by a forest is becoming more and more important.

A most simplified method to determine the gas discharge (flux) quantity per unit area from the ground will be described with reference to FIG. 15A. In this method, a container 101 having a small hole 102 is placed so as to cover the ground 100a and a concentration of a measuring object gas in an initial state in the container 101 is measured. After passing of a predetermined time, the gas concentration is again measured. Thus, by the concentration difference and ground covering area/volume of the container, the gas flux quantity can be assessed. In the figure, numeral 104 designates a gas collector and numeral 106 an analyzer.

Also, forest $CO_2$ flux measurement has recently begun to be actively carried out in many places. As shown in FIG. 15B, an observation tower 91 is installed in a forest 99. A current meter 51 having a good time-wise responsiveness (response ability) and a $CO_2$ densitometer 93 are mounted on the tower 91 so that atmospheric air observation is carried out. Results of the measurements are analyzed by the eddy correlation method to thereby obtain the forest $CO_2$ flux quantity (that is, the $CO_2$ absorption quantity by the forest). For example, the inventors here have heretofore reported continuous observations of $CO_2$ flux, as mentioned in Non-patent Document 1 below.

More concretely, as shown in FIG. 15B, as a current meter 51 for measuring a wind velocity, an ultrasonic current meter with a very high time-wise responsiveness is generally used. As to the $CO_2$ concentration measurement, while it is usual to use a closed path type $CO_2$ densitometer 96 using a sampling pipe 95, an open path type $CO_2$ meter, as shown by the $CO_2$ densitometer 93, with a high time-wise responsiveness using an infrared ray source (the measuring length is 1 m or less) also has recently begun to be used. In the figure, numeral 90 designates an observation room and numeral 19 an analyzer.

Moreover, if not a measurement of the gas flux itself, a regional momentum flux measuring technology using a laser has been developed and application thereof to the forest measurement is proceeding, wherein the regional momentum flux is defined as vertical directional transport properties of an atmospheric air mass (average density) being multiplied by a horizontal directional velocity component. This measuring technology, using a scintillation method, will be described. As shown in FIG. 15C, two observation towers 91, 92, being kept away from each other, are installed in the forest 99. A scintillation measuring unit 70 is mounted in a light source part 111 provided on one of the towers 91 and two laser beams are radiated therefrom so as to be transmitted above the forest 99 and received by a light receiving part 112 provided on the other of the towers 92. At the light receiving part 112, time-wise changes of respective laser transmission factors (scintillation) are measured. In the figure, numeral 90 designates an observation room, numeral 121a demodulator and numeral 122 an analyzer.

The basic construction of this prior art system comprises, as shown in FIG. 15D, a pair of scintillation measuring laser oscillators 113, 114 on the tower 91, a pair of light receivers 115, 116 on the tower 92 and the analyzer 122 provided in a measuring room 123. Two laser beams 113a, 114a transmitted through a measuring region 100 are received by the light receivers 115, 116, respectively, so that received light signals S101, S102 are sent to the analyzer 122. At the analyzer 122, an analysis 132 of variance and covariance is first carried out in order to determine an atmospheric turbulence state on the optical path (that is, an optical path turbulence analysis 131) and then a dissipation factor $\epsilon$ of kinetic energy or heat is obtained by an analyzing method 133 using the Monin-Obukhov similarity law (herein referred to as the MOS law). Also, a momentum flux or sensible heat flux 134 (including a latent heat flux also according to the case) is obtained.

By the way, it is generally known that, in the atmospheric boundary layer, turbulences are generated due to frictional actions and thermal actions on the ground surface and thus the upward transportation of various physical quantities are dominantly governed by turbulence transportation. According to the MOS law, it is shown that various statistical quantities of atmospheric variables in this region (average values, variances, covariances, spectra, etc.) become universal functions relative to z/L (z is a measuring height, L is a Monin-Obukhov length). Hence, in case this similarity law holds good, the atmospheric turbulence state (that is, in this case, the atmospheric density turbulences or the secondary density structure function $Dn^2$ corresponding to time-wise changes of the laser transmission factor) is measured and, based on the MOS law, the measurement results are sequentially analyzed (that is, the atmospheric turbulence state→kinetic energy spectra→energy dissipation factors) so that the momentum flux is obtained.

In order to obtain the momentum flux in this way, it is assumed that the MOS law is applicable to the portion above the forest and, using the method mentioned in Non-patent Document 2, the atmospheric turbulence state is analyzed by the laser scintillation state so that the momentum flux quantity on the optical path is obtained (scintillation method). Steps of this method are shown in FIGS. 16A and 16B.

Non-patent Document 1: "Introduction of $CO_2$ flux continuous observations in birch forests of the east foot of Mt. Asama" by Nakaya, O. et. al., 2002 CGER Flux Research Meeting (14 Nov., 2002), page 58.

Non-patent Document 2: "A displaced-beam scintillometer for line-averaged measurements of surface layer turbulence" by Thiermann, V., The 10th Symposium of Turbulence and Diffusion, 29 Sept.-2 Oct., 1992, Portland, Oreg., published by the American Meteorological Society, Boston, Mass., pages 244 to 247.

In measuring the gas flux using the above-mentioned prior art methods, however, there are shortcomings as follows:

(1) The gas densitometer of the state of the art does not necessarily satisfy the necessary conditions of the flux measurements.

For the gas concentration measurements used for the flux measurements, such as the forest $CO_2$ absorption measurements or the like, except the measurements considering no time-wise change of the flux quantity, as first shown as the prior art, the following characteristics are needed:

(i) High responsiveness

In order to detect the flux by the eddy correlation method, as quick a responsiveness (response time) as possible is demanded.

(ii) No influence by concomitants

In order to detect micro-components, it is demanded that there is given no influence by substances other than the object gas to be measured.

(iii) Measurement stability

As long time continuous measurements are needed, measurement stability is demanded.

That is, in the closed path type gas densitometer 96 of the sampling method that is generally used, there is caused a measurement delay or dilution effect for a structural reason. Hence, there is a problem in the responsiveness (response time).

Also, as the concomitants, such as $H_2O$ and solid particles, give influences, a pre-treatment (dehumidifying, dedusting) is always needed and this makes enhancement of the responsiveness (response time) difficult.

Also, in the open path type gas densitometer 93 that has begun to be gradually used for the purpose of improving the responsiveness (response time), an infrared ray source having a large oscillation width is used as the light source. Hence, there is easily given a large influence by the concomitant gas, especially by $H_2O$. Also, there is a problem in the measuring stability for reason of the light source.

(2) Regional continuous gas concentration measurements are difficult.

That is, in the presently used closed path type gas densitometer 96, the measuring range is limited to the region in the vicinity of the sampling position. Also, in the open path type gas densitometer 93, because of the light source problem, the measuring length thereof is at most 1 m or less. Hence, by the prior art systems, measurements of 1 m or more or, for example, measurements of regional gas concentration changes of such size as 10 m, 100 m or 1 km are difficult.

Even by the prior art systems, if a multiplicity of arrayed measuring devices are used, regional gas concentration measurements will be theoretically possible. Nevertheless, if a multiplicity of measuring devices are arranged, the existence itself of these devices becomes an obstacle that will change the state of the measuring region (concentration, flux or the like). Thus, an accurate regional flux measurement will be impossible.

SUMMARY OF THE INVENTION

In order to solve the above-mentioned problems in the prior art, it is an object of the present invention to provide a gas flux measuring device that is appropriate for regional measurements of forest or the like, has no influence of concomitants, has a high responsiveness and is excellent in measuring stability.

In the Japanese patent application No. 2003-009785, etc., the inventors here have proposed a gas concentration monitoring system making use of a non-contacting gas concentration measuring technology of a wavelength modulation type, that is, a tunable diode laser absorption spectroscopy (hereinafter referred to as "TDLAS"), in which the light source is an ordinary temperature oscillating near-infrared diode laser. The technology of TDLAS is a measuring technology having a good measuring stability with advantages such that (i) the time-wise responsiveness ris excellent, (ii) no influence is given by concomitants (solid particles or the like), (iii) the wavelength is stable, etc. Thus, if the TDLAS is used such that (a) as a simple gas concentration measuring technology, the TDLAS combined with a current meter having a high time-wise responsiveness is applied to the flux measurements or (b) a laser beam of which wavelength or polarization plane is controllable so as to be used for the gas concentration measurements by the TDLAS is applied to the flux measurements, such gas flux measurements as can effectively solve the above-mentioned prior art problems will become possible. Noticing such function of the TDLAS, the inventors here have completed the present invention as mentioned below.

A gas flux measuring device according to the present invention includes a light source oscillating a laser beam of an absorption wavelength natural to a measuring object gas toward a measuring region. A laser output controller controls an output action of the light source. A wavelength modulation controller puts out a modulation signal for adding a modulation to an oscillation wavelength of the laser beam oscillated from the light source as well as putting out a reference signal synchronized with the modulation. A first light receiver receives the laser beam transmitted through the measuring region and puts out a signal corresponding to a received light strength thereof. A first direct current component detector removes an alternating current component as a modulation signal out of the signal put out from the first light receiver and puts out a direct current component of the received light strength. A first wavelength modulation demodulator detects, based on the reference signal from the wavelength modulation controller, an even number order harmonic component of the wavelength modulation signal added to the laser beam out of the signal put out from the first light receiver and puts out a signal in proportion to a concentration of the measuring object gas in the measuring region. An optical system distributes the laser beam oscillated from the light source to two or more portions. A reference cell enclose the measuring object gas of which the concentration is known and is arranged at such a position that the laser beam, distributed by the optical system so as not to be directed to the measuring region, is transmitted through the enclosed gas. A second light receiver receives the laser beam transmitted through the enclosed gas in the reference cell and puts out a signal corresponding to a received light strength thereof. A second direct current component detector removes an alternating current component as a modulation signal out of the signal put out from the second light receiver and puts out a direct current component of the received light strength. A second wavelength modulation demodulator detects, based on the reference signal from the wavelength modulation controller, an even number order harmonic component of the wavelength modulation signal added to the laser beam out of the signal put out from the second light receiver and puts out a signal in proportion to the concentration of the enclosed gas in the reference cell. A third wavelength modulation demodulator detects, based on the reference signal from the wavelength modulation controller, an odd number order harmonic component of the wavelength modulation signal added to the laser beam out of the signal put out from the second light receiver and puts out a laser wavelength fixing signal as a standard signal for fixing the laser beam wavelength to the absorption wavelength of the measuring object gas. An analyzer calculates, based on the signals put out from the first direct current component detector, first wavelength modulation demodulator, second direct current component detector and second wavelength modulation demodulator, the gas concentration and a solid particle concentration in the measuring region and puts out a calculation result thereof. An adder adds the modulation signal from the wavelength modulation controller to the laser wavelength fixing signal from the third wavelength modulation demodulator and puts out an addition signal thereof as an external control signal into the laser output controller. A temperature measuring means measures a temperature in the measuring region and puts out a signal corresponding to a measured value thereof into the analyzer and a pressure measuring means measures a pressure in the measuring region and puts out a signal corresponding to a measured value thereof into the analyzer.

A gas flux measuring device according to the present invention may be further characterized by any one of the following (1) to (5):

(1) The gas flux measuring device further includes a flow velocity measuring means directly measuring horizontal 2-directional flow velocity components and a vertical flow velocity component of a gas flow in the measuring region and putting out measurement signals thereof into the analyzer. The analyzer carries out an analysis based on the eddy correlation method using the signals inputted from the flow velocity measuring means and, by calculation using an analysis result thereof, obtains a momentum flux [vertical directional transport properties of a horizontal directional momentum of the entire measuring region (an atmospheric air average density multiplied by a horizontal wind velocity, for example)] in the measuring region, a concentration flux (vertical directional transport properties of only the measuring object gas) of the measuring object gas and the concentration of the measuring object gas.

(2) The gas flux measuring device further includes a second light source radiating a laser beam to the measuring region and a third light receiver receiving the laser beam radiated from the second light source and transmitted through the measuring region and putting out a signal corresponding to a received light strength thereof into the analyzer. The analyzer obtains, based on the signal inputted from the third light receiver, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

(3) The gas flux measuring device further includes a second light source oscillating a laser beam of the absorption wavelength natural to the measuring object gas toward the measuring region, a third light receiver receiving the laser beam oscillated from the second light source and transmitted through the measuring region and putting out a signal corresponding to a received light strength thereof and a third direct current component detector removing an alternating current component as a modulation signal out of the signal received from the third light receiver and putting out a direct current component of the received light strength into the analyzer. The analyzer obtains, based on the signal inputted from the third direct current component detector, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

(4) The gas flux measuring device further includes a polarization plane rotating device having the optical system distributing the laser beam oscillated from the light source to two or more portions and rotating a polarization plane of the laser beam of the one or more portions distributed by the optical system, a third light receiver receiving the laser beam of which polarization plane is rotated by the polarization plane rotating device and putting out a signal corresponding to a received light strength thereof and a third direct current component detector removing an alternating current component as a modulation signal out of the signal received from the third light receiver and putting out a direct current component of the received light strength into the analyzer. The analyzer obtains, based on the signal inputted from the third direct current component detector, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

(5) The gas flux measuring device further comprises a polarization plane rotating device having a Faraday rotator that is externally controlled and rotates a polarization plane of the laser beam oscillated from the single light source. A polarization plane modulation controller controls a rotation angle of the Faraday rotator so as to change over the laser polarization plane between a vertical polarization and a horizontal polarization with a predetermined period. A first polarization plane demodulator detects, based on a strength modulation reference signal from the polarization plane modulation controller, a signal synchronized with a polarization plane modulation out of the signal put out from the first light receiver and puts out a signal in proportion to a received light strength of a vertically polarized laser beam transmitted through the measuring region as a measuring region laser absorption quantity signal into the analyzer. A second polarization plane demodulator detects, based on the strength of the modulation reference signal from the polarization plane modulation controller, a signal synchronized with the polarization plane modulation out of the signal put out from the first light receiver and puts out a signal in proportion to a received light strength of a horizontally polarized laser beam transmitted through the measuring region as a measuring region laser absorption quantity signal into the analyzer. A third polarization plane demodulator detects, based on the strength of the modulation reference signal from the polarization plane modulation controller, a signal synchronized with the polarization plane modulation out of the signal put out from the first light receiver and puts out a signal in proportion to a received light strength of the laser beam transmitted through the measuring region as a concentration measurement signal into the analyzer. The analyzer obtains, based on the signals inputted from the first, second and third polarization plane demodulators, time-wise changes of a laser transmission factor, obtains, based on these time-wise changes of the laser transmission factor, time-wise changes of a gas density, carries out an analysis based on the Monin-Obukhov similarity law in order to grasp a turbulence state of the measuring object gas using the time-wise changes of the gas density and obtains, by calculation using an analysis result thereof, a momentum flux in the measuring region, a concentration flux of the measuring object gas and the concentration of the measuring object gas.

In the present description, the term "momentum flux" means vertical directional transport properties of a horizontal directional momentum of the entire gas existing in the measuring region, wherein the horizontal directional momentum is, for example, an atmospheric air average density being multiplied by a horizontal directional wind velocity. Also, the term "gas flux" means vertical directional transport properties of only the measuring object gas in the measuring region.

As to the combination of the wavelength modulation TDLAS and the scintillation method, the following two cases can be named:

(i) Combination of a TDLAS device and a scintillation measuring device For example, as shown in FIGS. 7(a) and (b), a regional gas concentration measuring device by the wavelength modulation TDLAS and a regional momentum flux measuring device by the scintillation method are combined and respective measurement results thereof are incorporated together based on the MOS law and thereby the regional gas flux measurement is enabled.

(ii) Combination in which the TDLAS gas concentration measuring technology is directly added with the scintillation method.

For example, as shown in FIGS. 9(a) and (b), 11(a) and (b) and 13(a) and (b), the wavelength modulation TDLAS is added with the function of the scintillation method and thereby the regional gas flux measuring device by a single unit is enabled.

Next, the steps to obtain the momentum flux by the scintillation method are shown in FIGS. 16A and 16B. The basic principle for obtaining the momentum flux by the scintillation method is described in detail in the Non-patent Document 2. While the expressions of the steps shown in FIGS. 16A and 16B are not necessarily the same as those mentioned in the Non-patent Document 2, the basic concept thereof is the same.

When the laser beam is transmitted through the measuring region, if the gas in that region (the atmospheric air) is turbulent, the laser beam is slightly bent by the changes of the refractive index and thereby glittering of the laser beam (laser scintillation) can be measured at the light receiving part. In the scintillation method, as shown in FIG. 16A, this glittering is measured at two light receiving parts and, by the variance (B1, B2) and covariance (B) of respective data, the minimum unit (internal scale) Lo, momentum energy dissipation rate $\epsilon$ and degree of changes of the air density $\rho$ (density structure function) $Cn^2$ of the atmospheric turbulences are obtained.

The results thereof are analyzed based on the MOS law and using the equations shown in FIG. 16B, the air friction velocity $u^*$ is obtained. Then, using the result thereof and the air density $\rho$, the momentum flux M $[=\rho \cdot (u^*)^2]$ is obtained.

Next, the steps to obtain the gas flux will be described with reference to FIGS. 17A and 17B.

Like the usual measurements by the scintillation method, the internal scale Lo, momentum energy dissipation rate $\epsilon$ and density structure function $Cn^2$ are obtained based on the result of the laser scintillation measurements. Also, as shown in FIG. 17A, the concentration g of the measuring object gas in the measuring region is obtained by the TDLAS. By the result thereof, the degree of changes of the measuring object gas in the measuring region (gas concentration structure function) is obtained. Likewise, by the result of the temperature measurements, the temperature structure function $Cr^2$ is obtained.

The results of the above steps are analyzed based on the MOS law and, using the equations shown in FIG. 17B, the friction specific concentration $G^*$ of the air is obtained. Then, using the result thereof and the friction velocity $u^*$ of the air and the air density $\rho$, the concentration flux G ($=\rho \cdot u^* \cdot G^*$) of the measuring object gas is obtained.

According to the present invention, not only a gas flux measuring technology that can solve the prior art problem and enhance the measuring accuracy is realized but also a real time measuring of the regional gas flux that has so far been impossible by the combination of the conventional technologies becomes possible. Thus, as compared with the method combining the conventional methods, the environmental measurements or leakage monitoring using the present invention can realize a large reduction of work or cost and finally, upgrading of forest administration or safety administration of various industrial plants can be realized.

Also, according to the present invention, the polarization plane of the laser beam is changed over between vertical polarization and horizontal polarization. Therefore, the number of the laser oscillators and the number of the light receivers can be reduced.

Also, according to the present invention, advantages, mentioned next, of the wavelength modulation TDLAS device as the gas concentration measuring device can be fully obtained:

(i) The time-wise responsiveness is excellent.

That is, as the wavelength modulation TDLAS measurement is an optical measurement, the gas sampling or pretreatment as conventionally needed becomes unnecessary and the regional gas flux measurement that has been impossible by the combination of conventional technologies becomes possible. Also, a real time measurement can be realized because of the excellent time-wise responsiveness.

As compared with the prior art optical measuring method, the concentration measuring sensitivity by the wavelength modulation is largely enhanced, and even if the measuring time constant is reduced (or the time-wise responsibility is enhanced), measurement of the gas flux with a sufficient sensitivity becomes possible.

(ii) There is no influence of concomitants.

That is, as the laser having a very narrow wavelength line width as the light source is used, there is no influence by the concomitant gas. Also, by the wavelength modulation measurement, influence by the solid particles can be eliminated. Hence, measurements free of influence by dirt and free of obstruction by bad conditions, such as a rainy weather, can be realized.

(iii) The measurement stability is excellent.

That is, in the present invention, the wavelength modulation is carried out by plural steps and thereby the enhancement of the measurement stability is verified. Moreover, as the wavelength modulation TDLAS is of the optical measurement using the laser, the real time measurement of the regional gas concentration, which has been very difficult using the conventional gas concentration measuring technology, becomes possible. Thus, by combining this wavelength modulation TDLAS technology with the regional momentum flux measuring technology using the scintillation method, a real time measurement of the regional gas flux becomes possible.

BRIEF DESCRIPTION OF THE DRAWINGS

FIG. 16B is a flow chart showing a continuation of the steps of FIG. 16A.

FIG. 17B is a flow chart showing a continuation of the steps of FIG. 17A.

DETAILED DESCRIPTION OF THE INVENTION

Herebelow, the present invention will be described more concretely based on the embodiments with reference to the appended drawings.

Basic Construction of Gas Concentration Measurements

Figure 1:
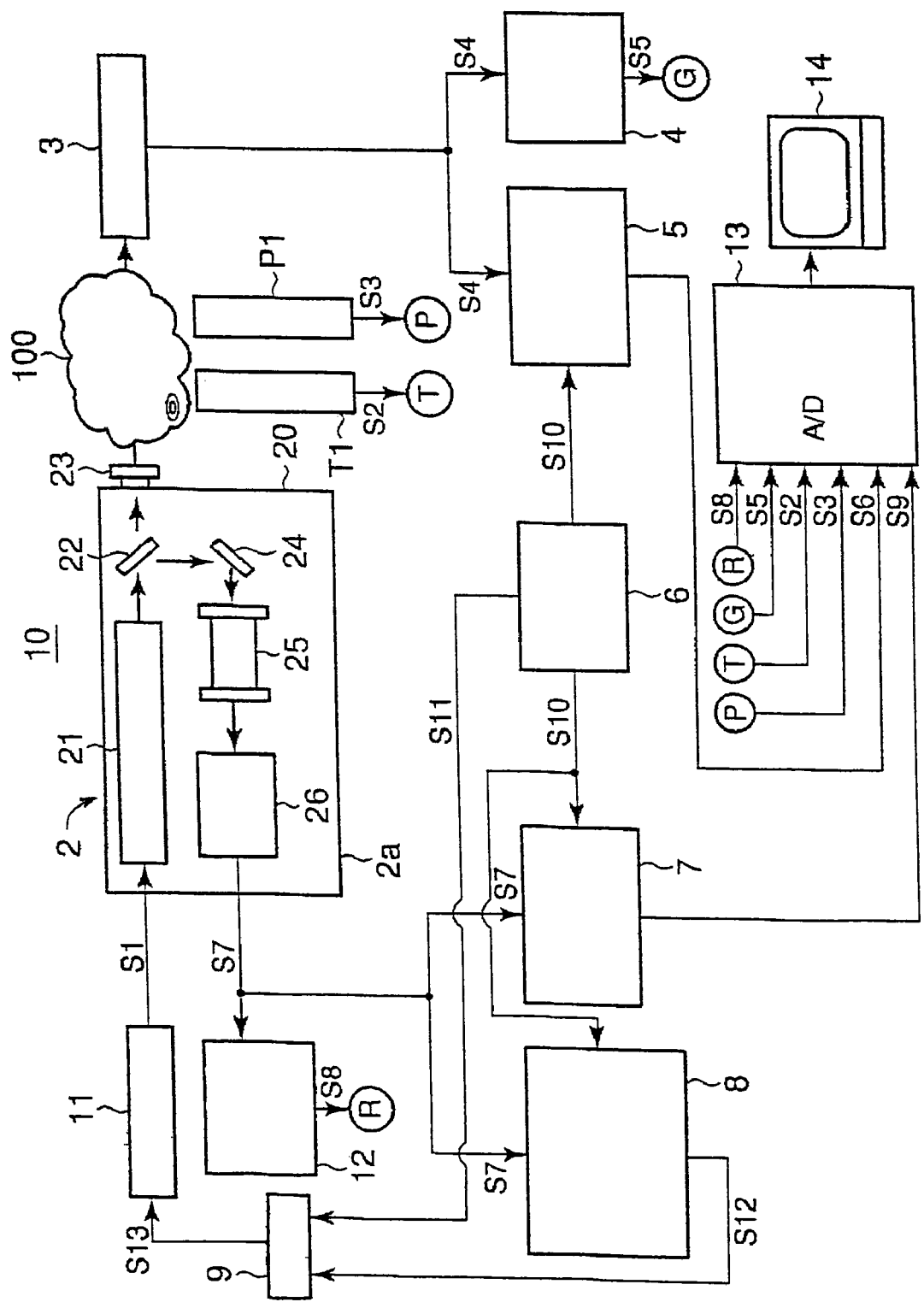
FIG. 1 is a block diagram showing a basic gas concentration measuring device to be used in a gas flux measuring device according to the present invention.

First, a basic construction of a gas concentration measuring device using the TDLAS to be used in the gas flux measuring device of the present invention will be described with reference to FIG. 1. In FIG. 1, a gas concentration measuring device 10 comprises a light source part 2, light receiver 3 for measuring purposes, direct current component detector 4 for measuring purposes, direct current component detector 12 for reference purposes, wavelength modulation demodulator 5 for concentration measuring purposes, wavelength modulation controller 6, wavelength modulation demodulator 7 for concentration calibrating purposes, wavelength modulation demodulator 8 for laser wavelength fixing signal purposes, adder 9, LD controller (laser output controller) 11, A/D converter 13 and computer 14 as an analyzing part. The light source part 2 has its outer periphery covered by an optical system container 2a having excellent weather resistance. Within the light source part 2, there are provided a semi-conductor laser beam source 21, reference cell 25, half mirror 22 transmitting a portion of the laser beam toward an optical window 23 as well as reflecting a portion of the laser beam, mirror 24 reflecting the laser beam reflected by the half mirror 22 toward the reference cell 25 and light receiver 26 for reference purposes receiving the laser beam from the reference cell 25.

The semi-conductor laser beam source 21 is provided within an LD module together with a Peltier element that carries out a temperature adjustment of the laser element. The semi-conductor laser element is connected to a drive circuit of the LD controller 11 so that the temperature and electric current thereof are controlled. An oscillation signal S1 sent to the laser beam source 21 from the LD controller 11 is applied with a feedback control by a signal S13 from the adder 9. It is to be noted that, in the present embodiment, while the light source is described as the laser beam source 21 using the semi-conductor laser element, the light source of the present invention is not limited to the semi-conductor laser element but all other laser oscillators that are capable of wavelength modulation can also be employed, or even in the case of light or electromagnetic wave devices other than the laser, if they are capable of wavelength modulation, they are all applicable. Also, the LD controller 11 may be either of a manual control or of an external control.

A temperature indicator T1 and pressure indicator P1 are provided in a measuring region 100 so that a measured temperature signal S2 and measured pressure signal S3 are sent to the computer 14 as the analyzing part via the A/D converter 13.

The light receiver 3 for measuring purposes purpose as a first light receiver is arranged having its optical axis coincide with an optical axis of the light source part 2 so as to receive the laser beam transmitted through the measuring region 100 that includes the measuring object gas and particles as objects to be measured. The direct current component detector 4 for measuring purposes as a first direct current component detector and the wavelength modulation demodulator 5 for concentration measuring purposes as a first wavelength modulation demodulator are provided downstream of the first light receiver 3. The first direct current component detector 4 removes an alternating current component as a modulation signal out of a signal S4 put out from the first light receiver 3 and puts out a direct current component signal S5 of a received light strength into the computer 14.

Based on a reference signal S10 from the wavelength modulation controller 6, the first wavelength modulation demodulator 5 detects an even number order harmonic component of the wavelength modulation signal added to the laser beam out of the signal S4 put out from the first light receiver 3 and puts out a signal S6 in proportion to the concentration of the measuring object gas in the measuring region 100.

The wavelength modulation controller 6 is provided upstream of the first wavelength modulation demodulator 5, the wavelength modulation demodulator 7 for concentration calibrating purposes as a second wavelength modulation demodulator and the adder 9, and puts out a wavelength modulation reference signal S10 to the first and second wavelength modulation demodulators 5, 7, respectively, and also puts out a wavelength modulation signal S11 to the adder 9.

In the reference cell 25, the measuring object gas ($CO_2$ gas, for example) of which concentration is known is enclosed and the reference cell 25 is arranged at such a position that the laser beam that has been distributed by the optical system (the half mirror 22 and mirror 24) so as not to be directed to the measuring region 100 is transmitted through the enclosed gas.

The light receiver 26 for reference purposes, as a second light receiver provided downstream of the reference cell 25, receives the laser beam that has been transmitted through the enclosed gas in the reference cell 25 and puts out a signal S7 corresponding to a received light strength thereof into the direct current component detector 12 for reference purpose as a second direct current component detector.

The second direct current component detector 12 removes an alternating current component as a modulation signal out of the signal S7 put out from the second light receiver 26 and puts out a direct current component signal S8 of the received light strength into the computer 14.

Based on the reference signal S10 from the wavelength modulation controller 6, the wavelength modulation demodulator 7 for concentration calibrating purpose as a second wavelength modulation demodulator detects an even number order harmonic component of the wavelength modulation signal added to the laser beam out of the signal S7 put out from the second light receiver 26 and puts out a signal S9 in proportion to the concentration of the enclosed gas in the reference cell 25 into the computer 14.

Based on the reference signal S10 from the wavelength modulation controller 6, the wavelength modulation demodulator 8 for laser wavelength fixing signal purpose as a third wavelength modulation demodulator detects an odd number order harmonic component of the wavelength modulation signal added to the laser beam out of the signal S7 put out from the second light receiver 26 and puts out a laser wavelength fixing signal S12 as a standard signal for fixing the laser wavelength to an absorption wavelength of the measuring object gas into the adder 9.

Based on the signals S2, S3, S5, S6, S8 and S9 put out from the temperature indicator T1, pressure indicator P1, first direct current component detector 4, first wavelength modulation demodulator 5, second direct current component detector 12 and second wavelength modulation demodulator 7, respectively, the computer 14 as the analyzing part calculates the gas concentration and solid particle concentration in the measuring region 100 and the result of the calculation is recorded as well as is put out to be displayed on a display screen.

The adder 9 adds the laser wavelength fixing signal S12 from the third wavelength modulation demodulator 8 to the modulation signal S11 from the wavelength modulation controller 6 and puts out an addition signal S13 thereof into the LD controller (laser output controller) 11 as an external control signal.

The calculation of the gas concentration is carried out as follows.

A standard gas of which gas concentration is known is previously enclosed or caused to flow in the reference cell 25 under a predetermined pressure. Firstly, the data of the known gas concentration in the reference cell 25, known optical length of the reference cell 25 and known optical length of the measuring region 100 are inputted into the computer 14 as the analyzing part. The computer 14 calls a predetermined equation from the memory and applies the three input data to respective parameters of the equation. Thereby, the gas concentration is obtained by calculation. The obtained values of the gas concentration are continuously recorded and, at the same time, the time-wise changing state thereof is put out to be displayed on a display screen.

The above describes the part of the device of the present invention that is in charge of the gas concentration measurement. In addition to the part of the gas concentration measurement, the device of the present invention comprises the part that is in charge of the flux measurement as follows.

Figure 2:
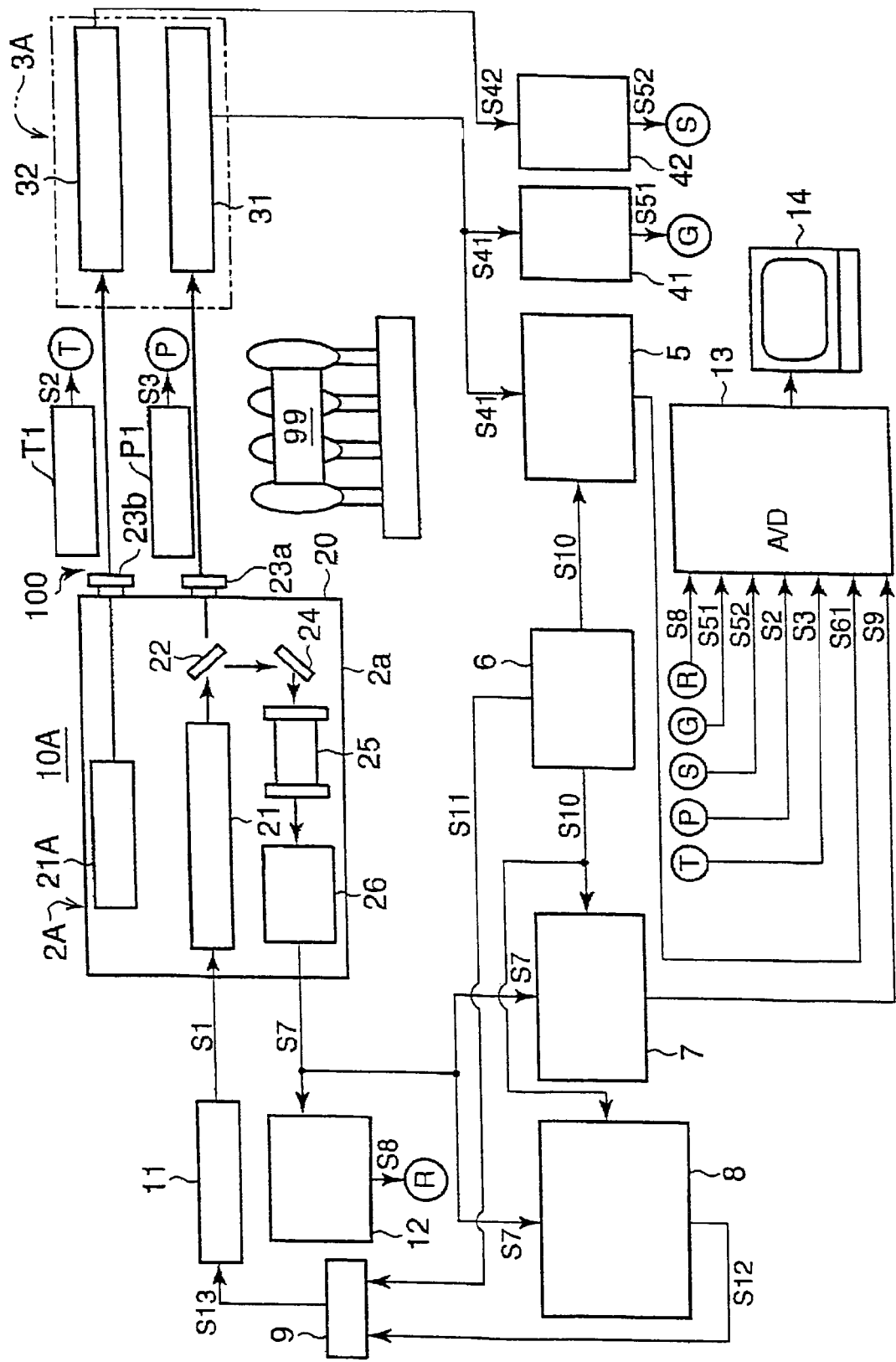
FIG. 2 is a block diagram showing a gas flux measuring device (comprising a combination of two laser beam sources and two light receivers) as an embodiment according to the present invention.

Gas flux measurement 1 by combination of two light sources with two light receivers for measuring purposes FIG. 2 is a block diagram showing an entire construction of a gas flux measuring device 10A according to the present invention as one embodiment. It is to be noted that as to the portions of the present gas flux measuring device 10A which are the same as those of the above gas concentration measuring device 10, repetitive descriptions will be omitted.

A light source part 2A of the gas flux measuring device 10A includes a laser beam source 21A as a second light source in addition to the semi-conductor laser beam source 21 as a first light source. An optical system container 2a has two optical windows 23a, 23b, arranged side by side, so that an oscillated laser beam of the first light source 21 is radiated to the measuring region 100 through the one optical window 23a and an oscillated laser beam of the second light source 21A is radiated to the measuring region 100 through the other optical window 23b. The first and second light sources 21, 21A are so positioned relative to each other that optical axes of the two laser beams become substantially parallel with each other.

A light receiver 3A for measuring purposes comprises a first light receiver 31 and a third light receiver 32. The first light receiver 31 receives the laser beam oscillated from the first light source 21 and puts out a signal S41 thereof into a first direct current component detector 41. The third light receiver 32 receives the laser beam oscillated from the second light source 21A and puts out a signal S42 thereof into a third direct current component detector 42.

The third direct current component detector 42 removes an alternating current component as a modulation signal out of the received light signal S42 and puts out a signal S52 as an atmospheric turbulence component signal into the computer 14 as the analyzing part. In parallel therewith, the first direct current component detector 41 removes an alternating current component as a modulation signal out of the received light signal S41 and puts out a signal S51 as a measuring part received light strength signal into the computer 14.

Based on the reference signal S10 from the wavelength modulation controller 6, the wavelength modulation demodulator 5 for concentration measuring purpose as the first wavelength modulation demodulator detects an even number order harmonic component of the wavelength modulation signal added to the laser beam out of the signal S41 put out from the first light receiver 31 and puts out a signal S61 in proportion to the concentration of the measuring object gas in the measuring region 100.

Based on the signals S2, S3, S51, S52, S61, S8 and S9 put out from the temperature indicator T1, pressure indicator P1, first direct current component detector 41, first wavelength modulation demodulator 5, second direct current component detector 12, second wavelength modulation demodulator 7 and third direct current component detector 42, respectively, the computer 14 as the analyzing part calculates the gas concentration and solid particle concentration in the measuring region 100 based on the MOS law and, at the same time, calculates the momentum flux in the measuring region 100. The result of these calculations is continuously recorded as well as is put out to be displayed on a display screen. In the figure, numeral 99 designates a forest in the measuring region 100.

Figure 3:
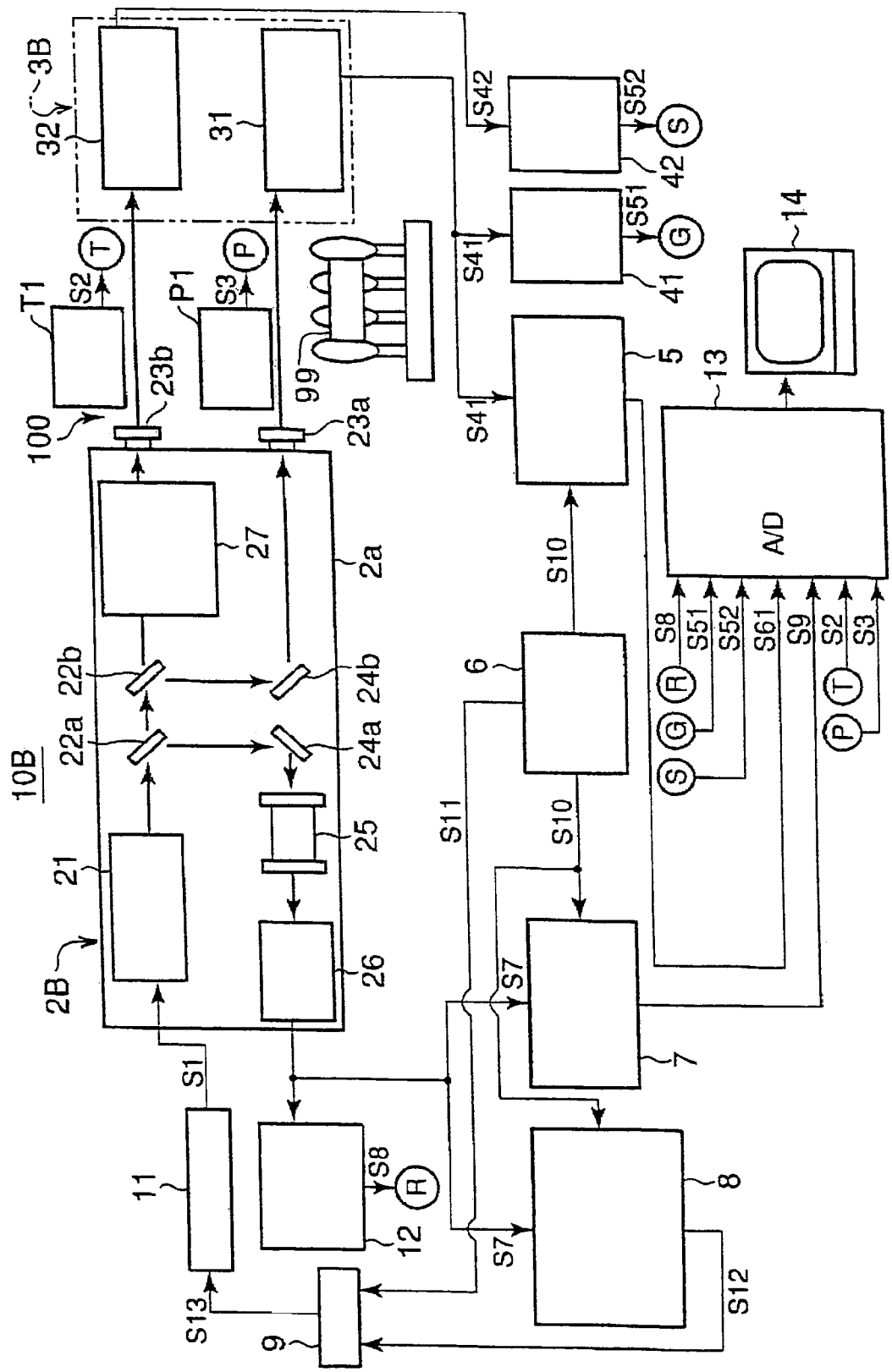
FIG. 3 is a block diagram showing a gas flux measuring device (comprising a combination of one laser beam source and two light receivers of a polarization plane modulation type) as another embodiment according to the present invention.

Gas Flux Measurement 2 by Combination of a Single Light Source with Two Light Receivers for Measuring Purposes FIG. 3 is a block diagram showing an entire construction of a gas flux measuring device 10B according to the present invention as another embodiment. It is to be noted that as to the portions of the present gas flux measuring device 10B same as those of the above devices 10, 10A, repetitive descriptions will be omitted.

A light source part 2B of the gas flux measuring device 10B comprises a polarization plane rotating device 27 having a polarization angle fixed to 90° and a laser beam distributing optical system including a first half mirror 22a and second half mirror 22b as well as two mirrors 24a, 24b. The first and second half mirrors 22a, 22b are provided between the light source 21 as the semi-conductor laser beam source and the polarization plane rotating device 27. The first half mirror 22a reflects a portion of the laser beam oscillated from the light source 21 to be distributed to the reference cell 25 via the mirror 24a. The second half mirror 22b reflects a portion of the laser beam transmitted through the first half mirror 22a so that this reflected laser beam is radiated to the measuring region 100 via the mirror 24b and the first optical window 23a. At the same time, the second half mirror 22b transmits a portion of the laser beam transmitted through the first half mirror 22a to be distributed to the polarization plane rotating device 27. The polarization plane rotating device 27 contains a Faraday rotator that rotates a vertically polarized light by an angle of 90° to be alternately converted to a horizontally polarized light. The laser beam applied with the polarization plane modulation by the polarization plane rotating device 27 is radiated to the measuring region 100 from the second optical window 23b. The optical system (22a, 22b, 24a and 24b) and the polarization plane rotating device 27 are so positioned relative to each other that optical axes of the two laser beams become substantially parallel with each other.

A light receiver 3B for measuring purpose comprises a first light receiver 31 and third light receiver 32. The first light receiver 31 receives the oscillated laser beam and puts out a signal S41 thereof into a first direct current component detector 41. The third light receiver 32 receives the laser beam applied with the polarization plane modulation and puts out a signal S42 thereof into a third direct current component detector 42.

The third direct current component detector 42 removes an alternating current component as a modulation signal out of the received light signal 42 and puts out an atmospheric turbulence component signal S52 into the computer 14 as the analyzing part. In parallel therewith, the first direct current component detector 41 receives an alternating current component as a modulation signal out of the received light signal S41 and puts out a signal S51 as a measuring part received light strength signal into the computer 14.

Based on the reference signal S10 from the wavelength modulation controller 6, the wavelength modulation demodulator 5 for concentration measuring purpose as the first wavelength modulation demodulator detects an even number order harmonic component of the wavelength modulation signal added to the laser beam out of the signal S41 put out from the first light receiver 31 and puts out a signal S61 in proportion to the concentration of the measuring object gas in the measuring region 100.

Based on the signals S2, S3, S51, S52, S61, S8 and S9 put out from the temperature indicator T1, pressure indicator P1, first direct current component detector 41, first wavelength modulation demodulator 5, second direct current component detector 12, second wavelength modulation demodulator 7 and third direct current component detector 42, respectively, the computer 14 as the analyzing part calculates the gas concentration and solid particle concentration in the measuring region 100 based on the MOS law and, at the same time, calculates the momentum flux in the measuring region 100. The result of these calculations is continuously recorded as well as is put out to be displayed on a display screen.

Figure 4:
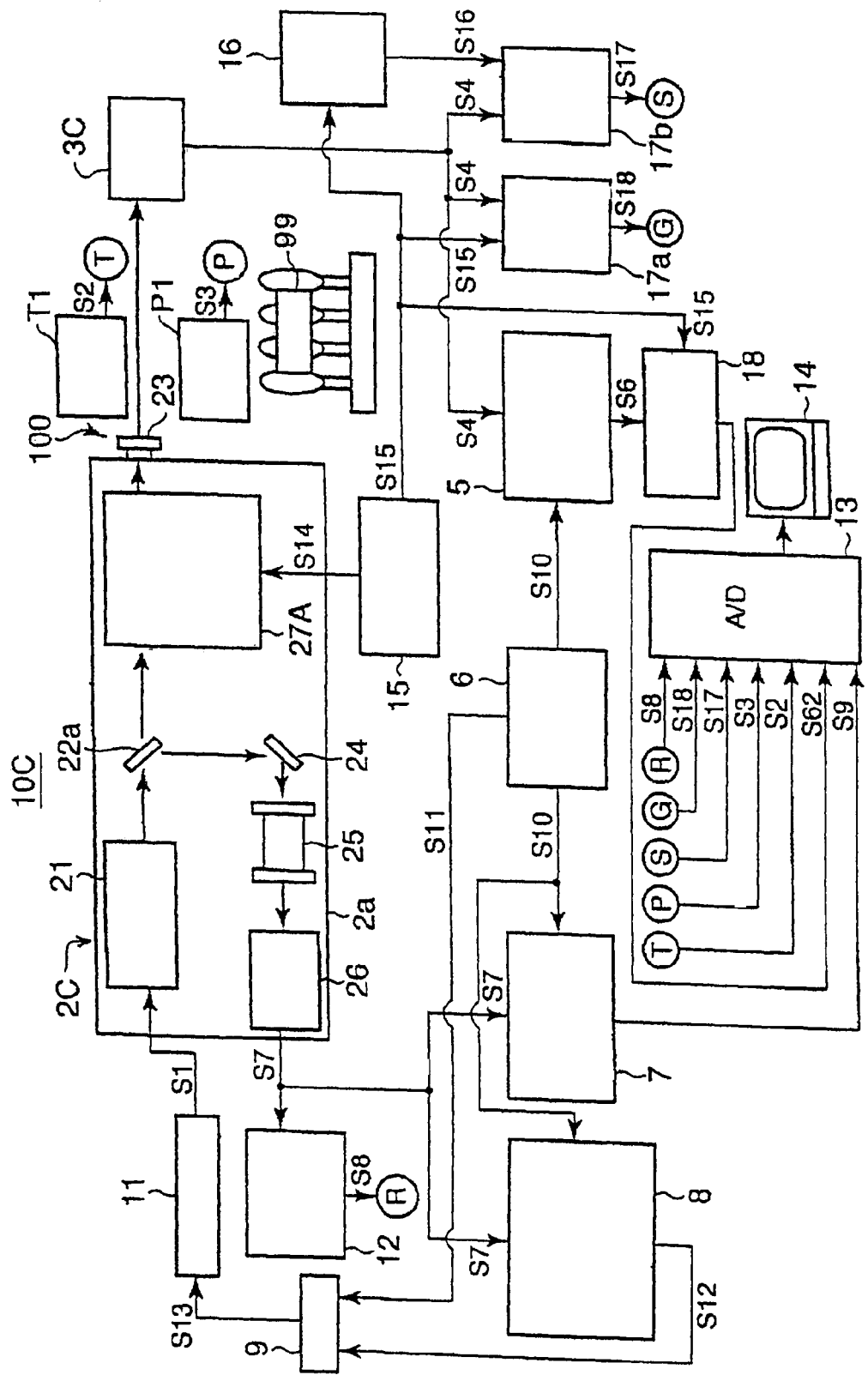
FIG. 4 is a block diagram showing a gas flux measuring device (comprising a combination of one laser beam source and one light receiver of an external control polarization plane modulation type) as still another embodiment according to the present invention.

Gas Flux Measurement 3 by Combination of a Single Light Source with a Single Light Receiver for Measuring Purposes FIG. 4 is a block diagram showing an entire construction of a gas flux measuring device 10C according to the present invention as still another embodiment. It is to be noted that as to the portions of the present gas flux measuring device 10C same as those of the above devices 10, 10A, 10B, repetitive descriptions will be omitted.

A light source part 2C of the gas flux measuring device 10C comprises an externally controlled polarization plane (modulation) rotating device 27A having a polarization angle of 0°/90°. The half mirror 22a reflects a portion of the laser beam oscillated from the single light source (the semi-conductor laser beam source) 21 to be distributed to the reference cell 25 via the mirror 24. At the same time, the half mirror 22a transmits a portion of the oscillated laser beam to be distributed to the externally controlled polarization plane rotating device 27A. The externally controlled polarization plane rotating device 27A is inputted with a modulation control signal S14 from a polarization plane modulation controller 15 provided outside so that change-overs between the vertically polarized light (0°) and the horizontally polarized light (90°) are carried out with a predetermined timing by the Faraday rotator. The laser beam applied with the polarization plane modulation by the externally controlled polarization plane rotating device 27A is radiated toward the measuring region 100 from the optical window 23 to be received by a light receiver 3C for measuring purpose. That is, in the device of the present embodiment, the single laser beam oscillated from the single light source 21 is applied with a timing control by which the vertically polarized light and the horizontally polarized light are alternately changed over and thereby the flux measurement and the concentration measurement are carried out at the same time.

The light receiver 3C puts out the received light signal S4 into a first polarization plane modulation demodulator 17a, second polarization plane modulation demodulator 17b and the first wavelength modulation demodulator 5, respectively.

The polarization plane modulation controller 15 puts out the modulation control signal S14 into the externally controlled polarization plane rotating device 27A and, at the same time, puts out a polarization plane modulation reference signal S15 into a signal phase converter 16, the first polarization plane modulation demodulator 17a and a third polarization plane modulation demodulator 18, respectively.

Upon receiving the polarization plane modulation reference signal S15 from the polarization plane modulation controller 15, the signal phase converter 16 converts a phase of the signal and puts out a phase conversion signal S16 thereof into the second polarization plane modulation demodulator 17b.

Based on the reference signal S10 from the wavelength modulation controller 6, the first wavelength modulation demodulator 5 detects an even number order harmonic component of the wavelength modulation signal added to the laser beam out of the received light signal S4 and puts out a signal S6 in proportion to the concentration of the measuring object gas in the measuring region into the third polarization plane modulation demodulator 18.

Upon receiving the polarization plane modulation reference signal S15 from the polarization plane modulation controller 15, the first polarization plane modulation demodulator 17a detects a signal synchronized with the polarization plane modulation out of the received light signal S4 and puts out a signal S18 in proportion to the received light strength of the vertically polarized laser beam that has been transmitted through the measuring region 100 as a measuring part laser beam absorption quantity signal into the computer 14 as the analyzing part.

Upon receiving the phase conversion signal S16 from the signal phase converter 16, the second polarization plane modulation demodulator 17b detects a signal synchronized with the polarization plane modulation out of the received light signal S4 and puts out a signal S17 in proportion to the received light strength of the horizontally polarized laser beam that has been transmitted through the measuring region as a measuring part laser beam absorption quantity signal into the computer 14.

Upon receiving the polarization plane modulation reference signal S15 from the polarization plane modulation controller 15, the third polarization plane modulation demodulator 18 detects a signal S62 in proportion to the strength of the received light signal S4 of the laser beam that has been transmitted through the measuring region 100 as a concentration measurement signal and puts it out into the computer 14.

Here, in order for the wavelength modulation reference signal S10 put out from the wavelength modulation controller 6 and the polarization plane modulation reference signal S15 put out from the polarization plane modulation controller 15 not to interfere with each other in the first wavelength modulation demodulator 5 or in the third polarization plane modulation demodulator 18, it is necessary that these modulation frequencies be different from each other. For example, as shown in FIG. 4, in the case where the third polarization plane modulation demodulator 18 is provided downstream of the first wavelength modulation demodulator 5, it is preferable that a frequency $\lambda 2$ of the polarization plane modulation reference signal S15 (100 Hz, for example) is set sufficiently lower than a frequency $\lambda 1$ of the wavelength modulation reference signal S10 (10 KHz, for example). On the other hand, in the case where these demodulators 5, 18 are reversely arranged, that is, if the third polarization plane modulation demodulator 18 is provided upstream of the first wavelength modulation demodulator 5, it is preferable that the frequency $\lambda 1$ of the polarization plane modulation reference signal S15 (1 MHz, for example) is set sufficiently higher than the frequency $\lambda 1$ of the wavelength modulation reference signal S10 (10 KHz).

Based on the signals S2, S3, S17, S18, S62, S8 and S9 put out from the temperature indicator T1, pressure indicator P1, first polarization plane modulation demodulator 17a, second polarization plane modulation demodulator 17b, third polarization plane modulation demodulator 18, second direct current component detector 12 and second wavelength modulation demodulator 7, respectively, the computer 14 as the analyzing part calculates the gas concentration and solid particle concentration in the measuring region 100 based on the MOS law and, at the same time, calculates the momentum flux in the measuring region 100. The result of these calculations is continuously recorded as well as is put out to be displayed on a display screen.

Actual Measurements

Measurement 1

Using a gas flux measuring device comprising a combination of a TDLAS type gas concentration measuring device and an ultrasonic current meter according to the present invention as still another embodiment, a $CO_2$ flux and concentration thereof are measured on a forest observation tower and the result will be described next as Measurement 1. It is to be noted that as to the parts and components of the present embodiment substantially the same as those of the above described embodiments, descriptions thereof will be omitted.

Figure 5:
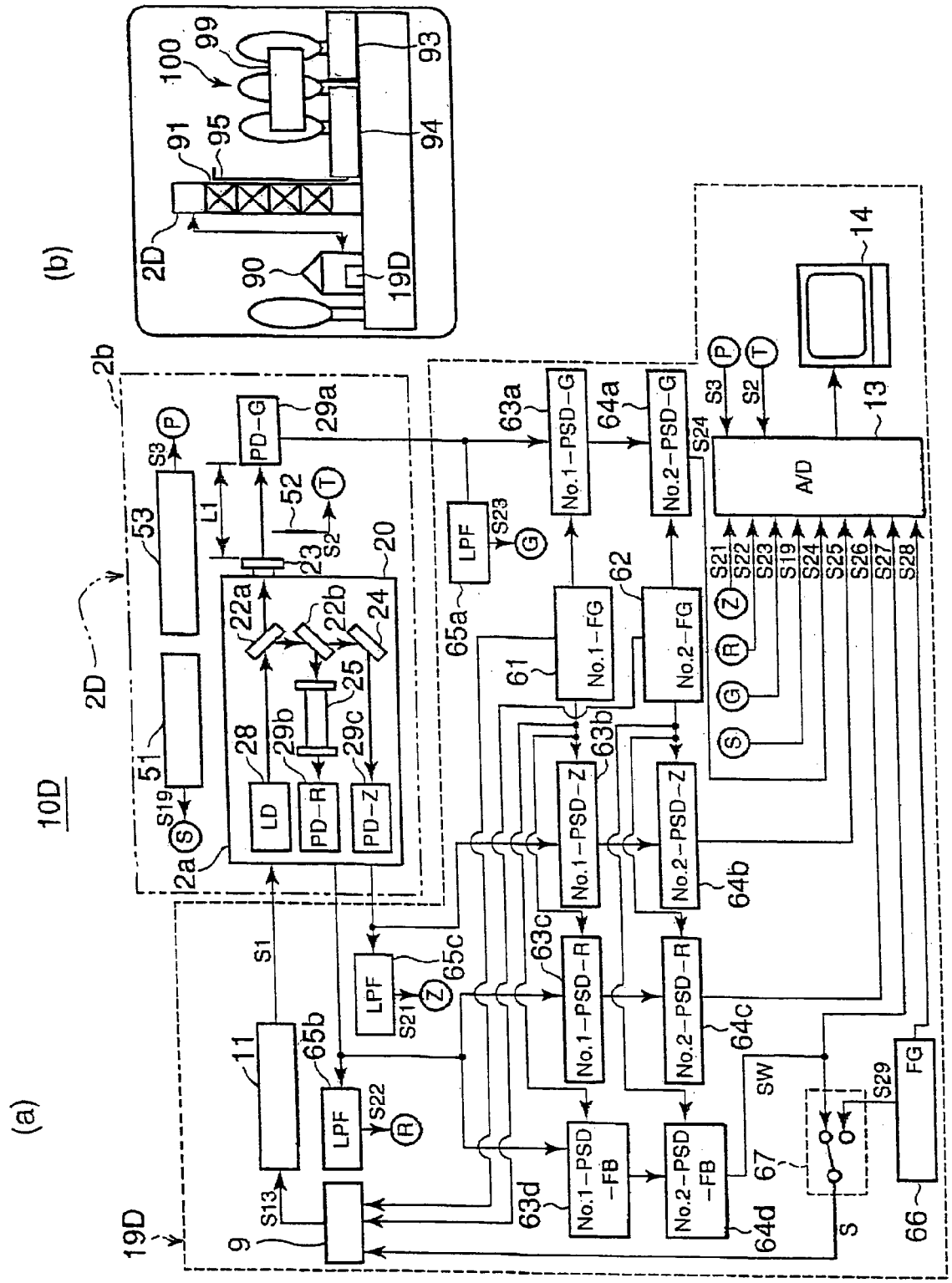
FIG. 5(a) is a block diagram showing a gas flux measuring device (used for Measurement 1: measuring a $CO_2$ flux on a forest observation tower) as still another embodiment according to the present invention
FIG. 5(b) is a schematic view showing a device arrangement thereof.

Here, in order to verify the gas flux measurement according to the present invention, as shown in FIGS. 5(a) and (b), a measuring part 2D, having a protective container 2b in which a gas concentration measuring device 20 of a wavelength TDLAS type and an ultrasonic current meter 51 are incorporated, is provided on a forest observation tower 91.

The result of measurements by these devices is analyzed by the eddy correlation method, so that the $CO_2$ flux on the forest observation tower 91 is obtained. It is to be noted that the gas in the measuring region 100 is introduced into the measuring part 2D on the forest observation tower 91 through a sampling pipe 95. Also, a $CO_2$ meter 93 and pretreatment device 94 are provided on a gas intake end side of the sampling pipe 95, so that a $CO_2$ concentration for comparison and confirmation purpose is actually measured as well as an intake gas is pretreated by a predetermined method. Moreover, a control/analyzing part 19D is provided in an observation room 90 near the tower 91.

As shown in FIG. 5(a), a gas flux measuring device 10D comprises the measuring part 2D and control/analyzing part 19D so that signals are transmitted or received between the measuring part 2D and the control/analyzing part 19D via a communication cable or radiotelegraph (not shown). While the gas concentration measuring device 20 of the wavelength TDLAS type incorporated in the measuring part 2D has substantially the same construction as the gas concentration measuring device 10 of the wavelength modulation TDLAS type shown in FIG. 1, in the present embodiment, in order to enhance the accuracy of the gas concentration measurement, there are additionally provided a double wavelength modulation mechanism (a first wavelength modulation waveform generator 61 and a second wavelength modulation waveform generator 62) in the control/analyzing part 19D and a concentration zero measuring part for monitoring a concentration zero point (a direct current detector 65c in the control/analyzing part 19D and a zero reference part 29c in the measuring part 2D). It is to be noted that in the respective blocks shown in FIG. 5(a), reference letters PSD designate a phase sensitive detector and, following the reference letters PSD, reference letter G designates a measuring part, reference letter R a reference part, reference letter Z a background $CO_2$ measurement and reference letters FB a wavelength fixing.

Concretely, the measuring part 2D provided on the forest observation tower 91 comprises a TDLAS optical system unit oscillating a laser beam as the gas concentration measuring device 20 of the wavelength TDLAS type, a light receiver (PD-G) 29a receiving the laser beam that has been transmitted through the measuring region 100 and an ultrasonic current meter 51.

The measuring part 2D in its entirety is covered by the protective container 2b. The TDLAS optical system unit 20 (or the wavelength TDLAS type gas concentration measuring device 20) in its entirety is covered by the optical system container 2a that is excellent in a weather resistance for the purpose of enhancing an anti-environment property. The optical system container 2a is fitted with the optical window 23 through which the laser beam is radiated. The light receiver (PD-G) 29a made of a photodiode is arranged so as to face to the optical window 23. An opening end of the sampling pipe 95 is introduced into the measuring part 2D to be positioned between the light receiver (PD-G) 29a and the optical window 23, so that the intake gas (the air in the forest 99) is supplied thereinto. In the present embodiment, a distance L1 from the optical window 23 to the light receiver (PD-G) 29a is set to about 2 m.

Next, the control/analyzing part 19D provided in the observation room 90 near the forest observation tower 91 comprises the LD controller 11 controlling the oscillated laser beam from a semi-conductor laser (LD) 28, first wavelength modulation waveform generator (No. 1-FG) 61/second wavelength modulation waveform generator (No. 2-FG) 62 both modulating the laser beam, direct current detectors (LPF) 65a to 65c functioning as mentioned below, first phase sensitive detectors (No. 1-PSD-G, Z, R, FB) 63 (63a to 63d)/second phase sensitive detectors (No. 2-PSD-G, Z, R, FB) 64 (64a to 64d) functioning as mentioned below, the A/D converter 13 taking all of the respective signals, the computer 14 (personal computer) analyzing A/D converted signals so that the $CO_2$ concentration and $CO_2$ flux in the air are analyzed and recorded and the adder 9 adding together the modulation signals from the first waveform generator (No. 1-FG) 61 and second waveform generator (No. 2-FG) 62 and the wavelength fixing signal from the second phase sensitive detector (No. 2-PSD-FB) 64d and putting out a signal as an external control signal into the LD control unit 11.

The direct current detectors (LPF) 65a to 65c function to detect the direct current component out of the received light signals from respective light receivers (PD-G, PD-R, PD-Z) 29a to 29c and put out received light strength signals S23, S22, S21. The first phase sensitive detectors (No. 1-PSD-G, Z, R, FB) 63 (63a to 63d) function, based on the reference signals from the first wavelength modulation waveform generator 61, to detect only such signals as synchronized with a double wave frequency component of the modulation frequency from the respective received light signals and put them out. The second phase sensitive detectors (No. 2-PSD-G, Z, R, FB) 64 (64a to 64d) function, based on the reference signals from the second wavelength modulation waveform generator (No. 2-FG) 62, to detect only such signals as synchronized with the double wave frequency component of the modulation frequency from the output signals from the first phase sensitive detectors 63.

Also, in the present embodiment, there are additionally provided a wavelength sweep waveform generator (FG) 66 sweeping the laser wavelength around the $CO_2$ absorption wavelength and a change-over switch (SW) 67 changing over the signal therefrom with the laser wavelength fixing signal.

The measuring part 2D comprises therein the ultrasonic current meter 51, a semi-conductor type pressure sensor 53 and a temperature sensor 52. The current meter 51 and sensors 52, 53 are provided near a blow-off port of the sampling pipe 91 and put out a measured flow velocity signal S19, measured temperature signal S2 and measured pressure signal S3, respectively, into the computer 14 as the analyzing part via the A/D converter 13.

The single semi-conductor laser (LD) 28 can adjust the laser oscillation wavelength to one of the absorption wavelengths of $CO_2$. The optical system comprises a first half mirror 22a, second half mirror 22b and reflecting mirror 24. The first half mirror 22a transmits a portion of the laser beam oscillated from the light source 28 to be distributed to the optical window 23 so that this laser beam is radiated toward the light receiver (PD-G) 29a for measuring purposes. At the same time, the first half mirror 22a reflects a portion of the oscillated laser beam to be distributed to the second half mirror 22b. The second half mirror 22b reflects a portion of the distributed laser beam to be further distributed to the reference cell 25 and, at the same time, transmits a portion of the distributed laser beam to be distributed to the zero reference part (PD-Z) 29c via the reflecting mirror 24. In the reference cell 25, $CO_2$ gas of a predetermined concentration ($CO_2$=1%, $N_2$=99%) is enclosed. The laser beam that has been transmitted through the reference cell 25 enters the light receiver (PD-R) 29b for reference purposes so that a received light signal is put out into a direct current detector (LPF) 65b of the control/analyzing part 19D. The direct current detector (LPF) 65b removes an alternating current component as a modulation signal from the received light signal and puts out a signal S22 thereof into the computer 14.

On the other hand, with the received light signal entering the direct current detector (LPF) 65c of the control/analyzing part 19D from the zero reference part (PD-Z) 29c, the direct current detector (LPF) 65c removes an alternating current component as a modulation signal from the received light signal and puts out the signal S21 thereof into the computer 14.

The light receiver (PD-G) 29a for measuring purpose puts out the received light signal into a direct current detector (LPF) 65a and first phase sensitive detector (No. 1-PSD-G) 63a, respectively, of the control/analyzing part 19D. With the received light signal entering the direct current detector (LPF) 65a, the direct current detector (LPF) 65a removes an alternating current component as a modulation signal from the received light signal and puts out the signal S23 thereof into the computer 14. Based on the wavelength modulation reference signal from the first wavelength modulation waveform generator (No. 1-FG) 61, the first phase sensitive detector (No. 1-PSD-G) 63a detects an even number order harmonic component of the wavelength modulation signal added to the laser beam out of the signal put out from the light receiver 29a for measuring purposes and puts out a signal in proportion to the concentration of the enclosed gas in the reference cell into a second phase sensitive detector (No. 2-PSD-G) 64a. Also, based on the wavelength modulation reference signal from the second wavelength modulation waveform generator (No. 2-FG) 62, a second phase sensitive detector (No. 2-PSD-G) 64a detects an odd number order harmonic component of the wavelength modulation signal added to the laser beam out of the signal put out from the light receiver 29a and puts out a signal S24 in proportion to the concentration of the enclosed gas in the reference cell into the computer 14.

In order for the laser oscillation wavelength to be slowly swept at the absorption spectrum that is natural to the measuring object gas, the wavelength sweep waveform generator (FG) 66 is constructed such that a ramp wave of frequency of 0.5 Hz or 0.01 Hz, for example, is applied to an injection current of the semi-conductor laser element. It is to be noted that in case where the changes of the gas concentration are to be measured for a long time, the sweep of the laser oscillation wavelength by the wavelength sweep waveform generator 66 is stopped and the laser oscillation wavelength is locked to a predetermined wavelength. The wavelength sweep waveform generator 66 puts out a wavelength sweep signal S28 into the computer 14.

For modulating the laser oscillation wavelength, the two wavelength modulation waveform generators 61, 62 are constructed such that sine waves of frequencies different from each other are doubly applied to the injection current of the semi-conductor laser element 28. For example, from the one wavelength modulation waveform generator 61, a sine wave of 10 KHz (f=10 KHz), for example, as a first modulation frequency f, is applied to the LD controller 11 via the adder 9 and from the other wavelength modulation waveform generator 62, a sine wave of 500 Hz (w=500 Hz=0.5 KHz), for example, as a second modulation frequency w, is applied to the LD controller 11 via the adder 9.

The adder 9 superposes a sweep signal S29 from the wavelength sweep waveform generator 66, modulation signals S25, S26 of the different frequencies f, w from the two wavelength modulation waveform generators 61, 62 and a third order differential demodulation signal S27 of the frequency 2+w from the phase sensitive detectors 63a to 63d, 64a to 64d of two steps and the result thereof is applied to the injection current of the semi-conductor laser element.

By the ramp wave having the sweep wavelength being applied to the injection current from the wavelength sweep waveform generator 66 as well as by the sine waves of the different frequencies f, w being doubly applied to the injection current from the wavelength modulation waveform generators 61, 62, the laser oscillation wavelength is doubly modulated by the two different frequencies f, w. As a result of this, the received light signal of the laser beam includes both the modulation frequencies f, w and harmonic components thereof. Hence, the signals are demodulated in the frequency of two times, that is, 20 KHz (2f), by the first phase sensitive detectors 63a to 63d and are then demodulated in the frequency of two times, that is, 1 KHz (2w), by the second phase sensitive detectors 64a to 64d. Thus, a fourth order differential signal (2f+2w) in which these demodulated signals are superposed is sent to the computer 14.

Also, the signals demodulated in the frequency of two times, that is, 20 KHz (2f), by the first phase sensitive detectors 63a to 63d are demodulated in the frequency w by the second phase sensitive detectors 64a to 64d. Thus, a third order differential signal (2f+w) in which these demodulated signals are superposed is sent to the adder 9 via the change-over switch 67. Based on this signal, the laser oscillation wavelength is applied with a feedback control to the absorption central wavelength of the measuring object gas.

The wind velocity on the tower 91 is measured by the ultrasonic current meter 51 and a wind velocity signal (S) thereof is put out into the control/analyzing part 19D of the observation room 90. As shown in FIGS. 5(a) and (b), the measuring region 100 includes the air on the tower 91 of a measuring length of 2 m (L1=2 m). Also, the pressure of the measuring region 100 is measured by a semi-conductor type pressure sensor 53 and a measured pressure signal S3 thereof is put out into the observation room 90. The temperature of the measuring region 100 is measured by a thermocouple (temperature sensor) 52 and a measured temperature signal S2 thereof is put out into the computer 14. In terms of the pressure or temperature, it is to be noted that, in place of using the sensors, a measurement by a laser may also be employed making use of the characteristic of the absorption spectrum of the measuring object gas.

In order to measure the absorption spectrum, a ramp wave of 0.5 Hz or 0.01 Hz, for example, is applied to the injection current by the wavelength sweep waveform generator (FG) 66 so that sweeping of the laser wavelength is slowly carried out. If concentration changes for a long time are to be measured, the laser wavelength is locked.

In the present Measurement 1, for the purpose of comparison, conventional measurements are also carried out as a comparison example 1 such that sampling of the air is done from substantially the same position as the measuring region of the present invention and the air is pretreated by the pretreatment device 94 and measured by the prior art $CO_2$ meter 93 so that the measurement result is analyzed by the eddy correlation method together with the measurement result of the ultrasonic current meter 51 and, at the same time, the $CO_2$ flux is measured.

Figure 6:
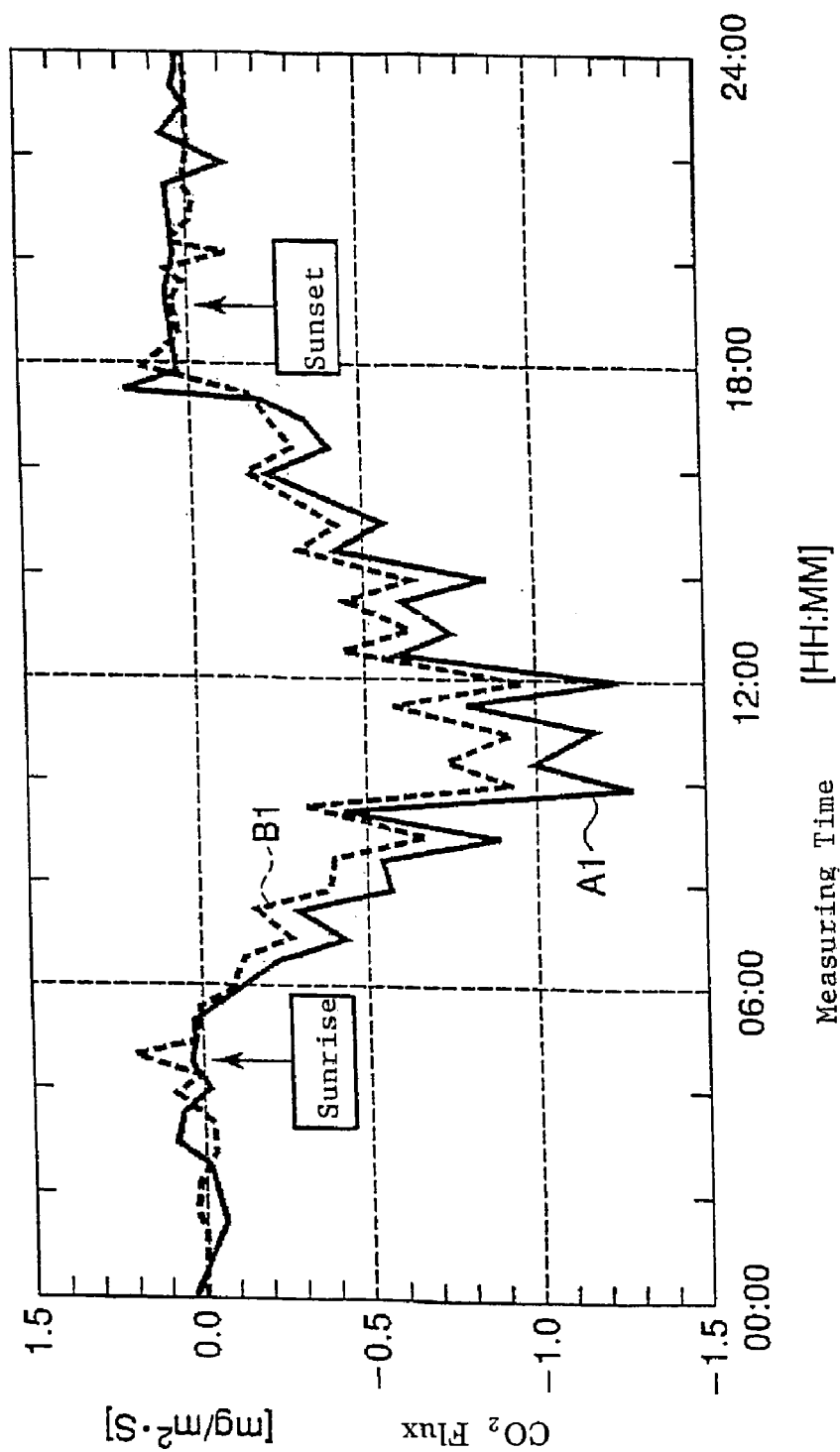
FIG. 6 is a characteristic diagram showing the result of Measurement 1 (measuring a forest $CO_2$ flux by the measuring device combined with an ultrasonic current meter).

FIG. 6 is a characteristic diagram showing the result of the Measurement 1, wherein the horizontal axis shows the measuring time and the vertical axis shows the measured $CO_2$ flux ($mg/m^2$ S). There, a solid line A1 shows the result of the Measurement 1 according to the device of the present invention and a broken line B1 shows the result of the comparison example 1 measured by a conventional device using the sampling method.

The results of both of the measurements are substantially the same, by which it is verified that the $CO_2$ flux measurement according to the present invention is feasible. Moreover, in circumstances such as immediately after sunrise or immediately after sunset, where the momentum flux largely changes from minus to plus by change-over of the photosynthesis/breathing of plants, while the measurement result of the present Measurement 1 (the characteristic line A1) clearly catches these changes, the measurement result of the conventional art (the characteristic line B1) does not necessarily catch such clear changes. This is considered to be the case because of the response delay of the prior art $CO_2$ meter 93 due to a dilution effect or the like. In this way, in the conventional device, quick changes in the measuring region cannot be sufficiently determine and there is a tendency that the actual flux quantity is underestimated. On the contrary, in the $CO_2$ flux measurement by the device of the present invention, quick changes in the measuring region can be precisely determine and the feasibility thereof is verified.

Measurement 2

Next, as Measurement 2, an example of measuring the regional $CO_2$ flux between two forest observation towers using a combination of the TDLAS regional gas concentration measuring device and the scintillation method according to the present invention as still another embodiment will be described with reference to FIGS. 7(a) and (b). It is to be noted that as to the parts and components of the present embodiment substantially the same as those of the above described embodiments, descriptions thereof will be omitted.

In the present Measurement 2, in order to verify the regional gas flux measurement according to the present invention, a wavelength TDLAS type gas concentration measuring device and a scintillation method type momentum flux measuring device, combined together, are provided on the forest observation towers and the result of measurements by these two devices are analyzed based on the MOS law, so that the regional $CO_2$ flux between the forest observation towers is measured.

Figure 7:
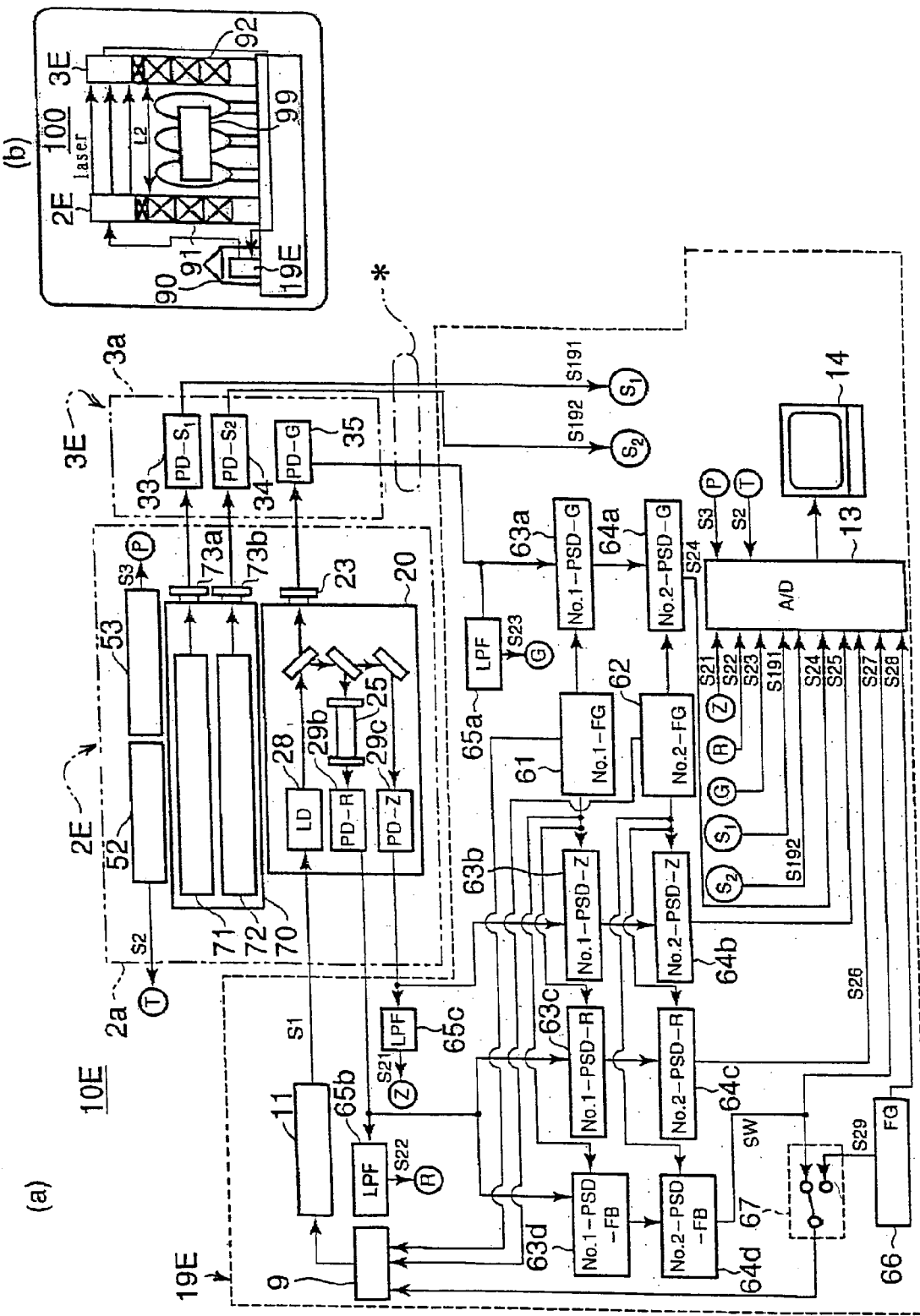
FIG. 7(a) is a block diagram showing a gas flux measuring device (used for Measurement 2: measuring a regional $CO_2$ flux between two forest observation towers) as still another embodiment according to the present invention
FIG. 7(b) is a schematic view showing a device arrangement thereof.
Figure 9:
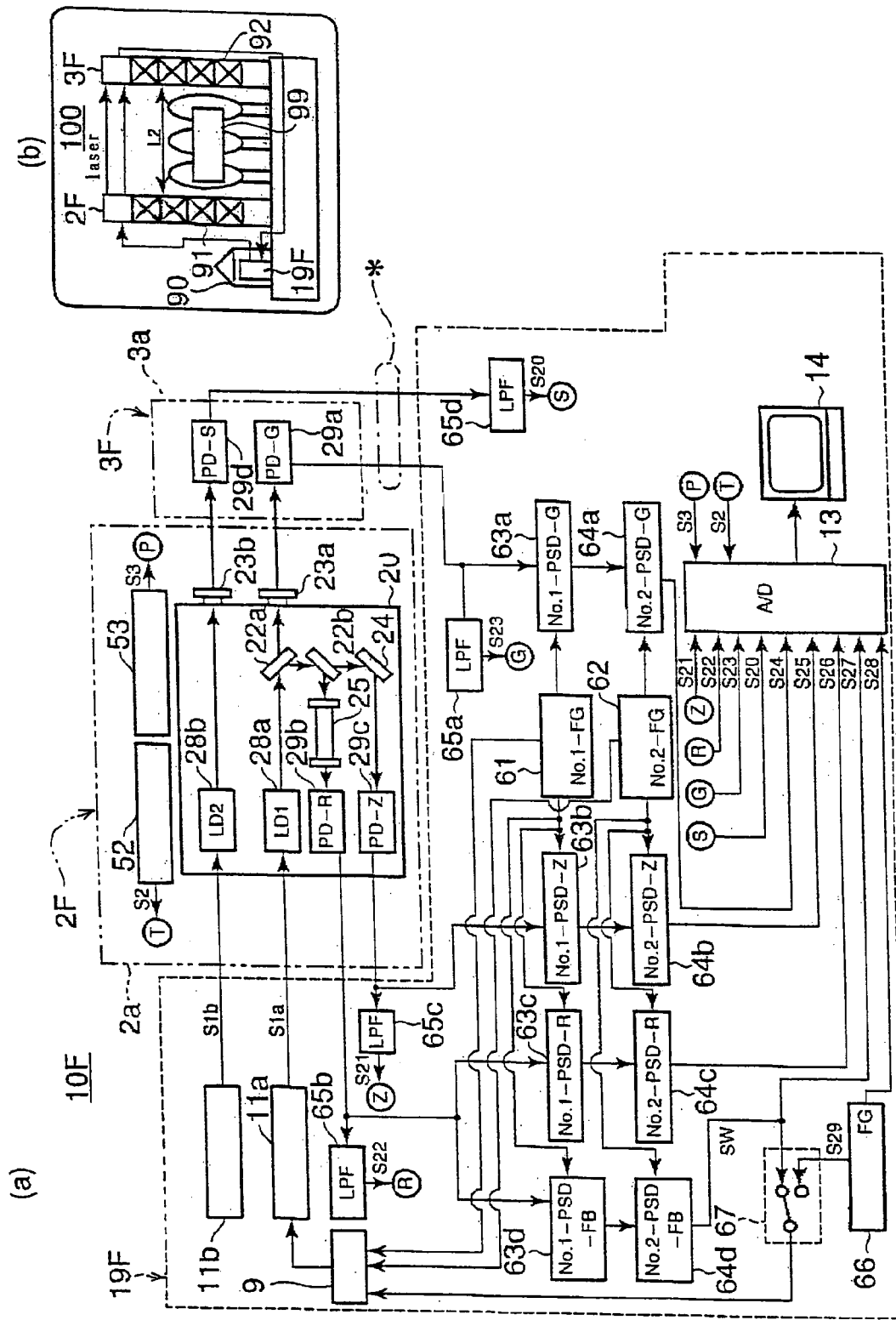
FIG. 9(a) is a block diagram showing a gas flux measuring device (used for Measurement 3 measuring a regional $CO_2$ flux between two forest observation towers) as still another embodiment according to the present invention and FIG. 9(b) is a schematic view showing a device arrangement thereof.
Figure 11:
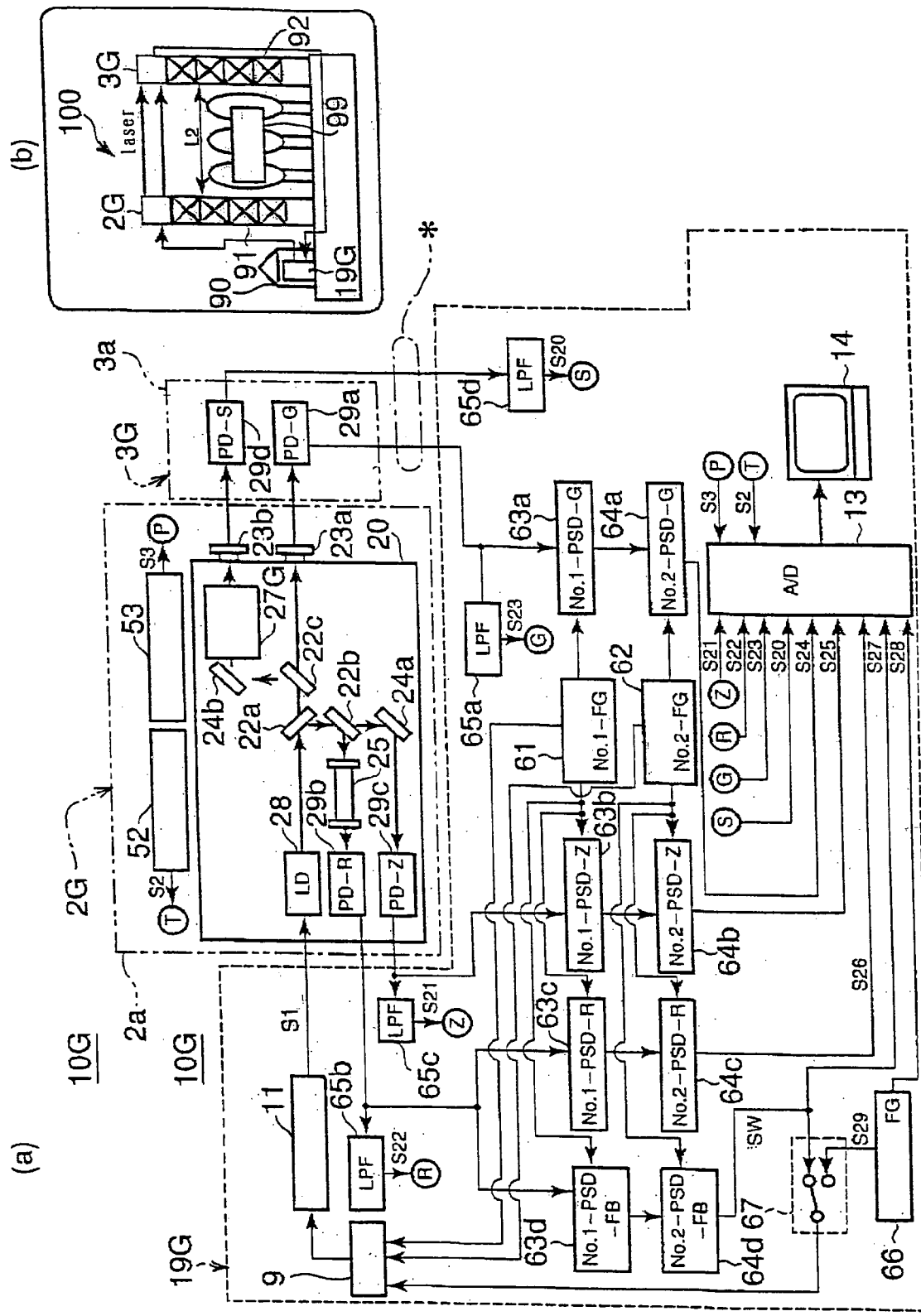
FIG. 11(a) is a block diagram showing a gas flux measuring device (used for Measurement 4: measuring a regional $CO_2$ flux between two forest observation towers) as still another embodiment according to the present invention
FIG. 11(b) is a schematic view showing a device arrangement thereof.
Figure 13:
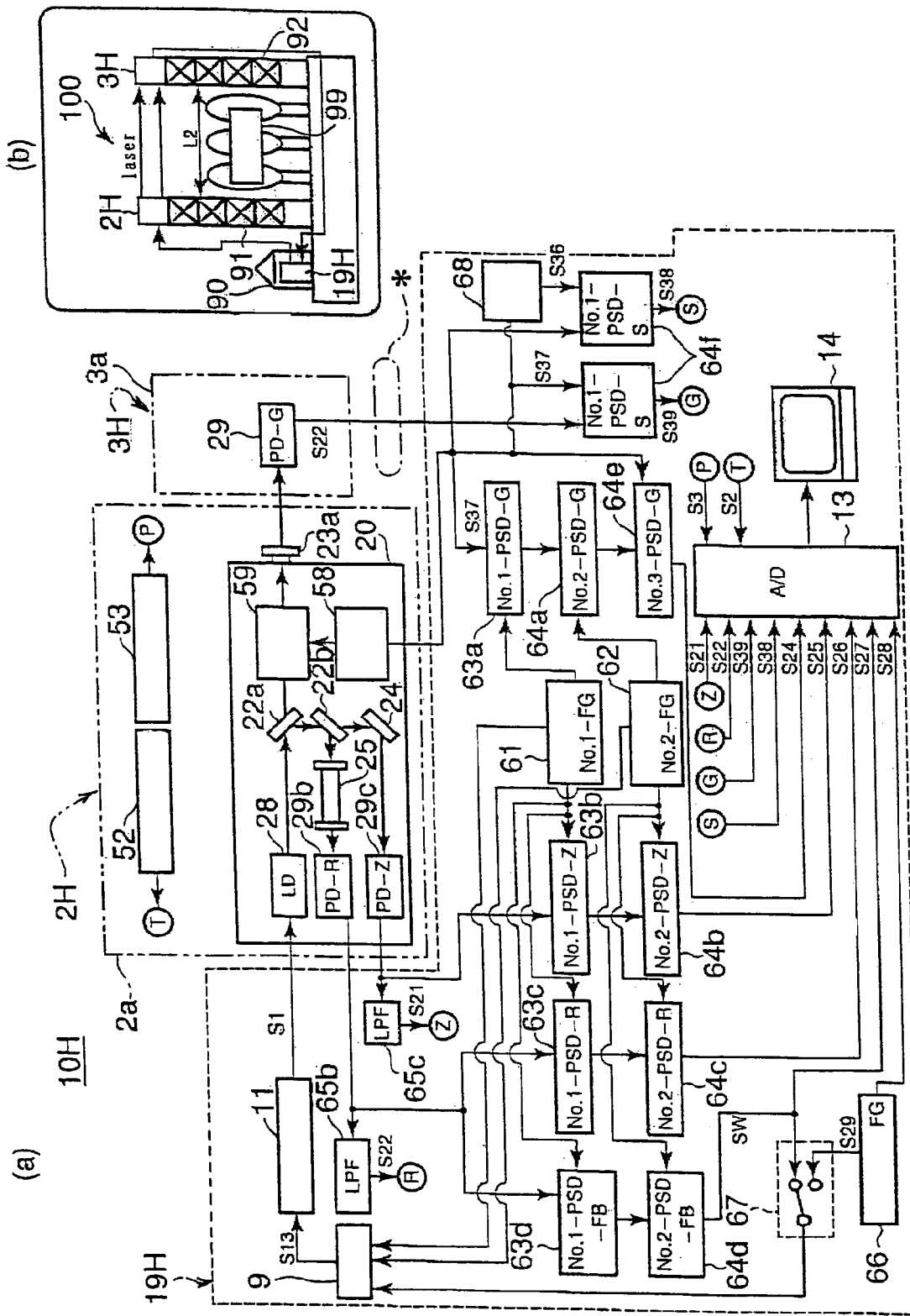
FIG. 13(a) is a block diagram showing a gas flux measuring device (used for Measurement 5: measuring a regional $CO_2$ flux between two forest observation towers) as still another embodiment according to the present invention
FIG. 13(b) is a schematic view showing a device arrangement thereof.

FIGS. 7(a) and (b) show a device system used for the present Measurement 2. Construction of a wavelength TDLAS type gas concentration measuring device system 2E including 19E is substantially the same as the device system 2D including 19D used for the Measurement 1 shown in FIGS. 5(a) and (b). Also, a control/analyzing part 19E provided in the observation room 90 is substantially the same as the control/analyzing part 19D of the Measurement 1 shown in FIGS. 5(a) and (b). However, in the system of the present Measurement 2, because of the regional gas concentration measurement, a measuring length L2 is set to a very long distance such that L2=81 m which equals the distance between two forest observation towers 91, 92. It is to be noted that in the respective blocks shown in FIG. 7(a), reference letters FG designate a waveform generator, reference letters PSD a phase sensitive detector, reference letter G a measuring part, reference letter R a reference part, reference letter Z a background $CO_2$ measurement, reference letters FB a wavelength fixing and reference letter S a scintillation measuring part. The same applies also to the below mentioned systems shown in FIGS. 9, 11 and 13.

Figure 15A:
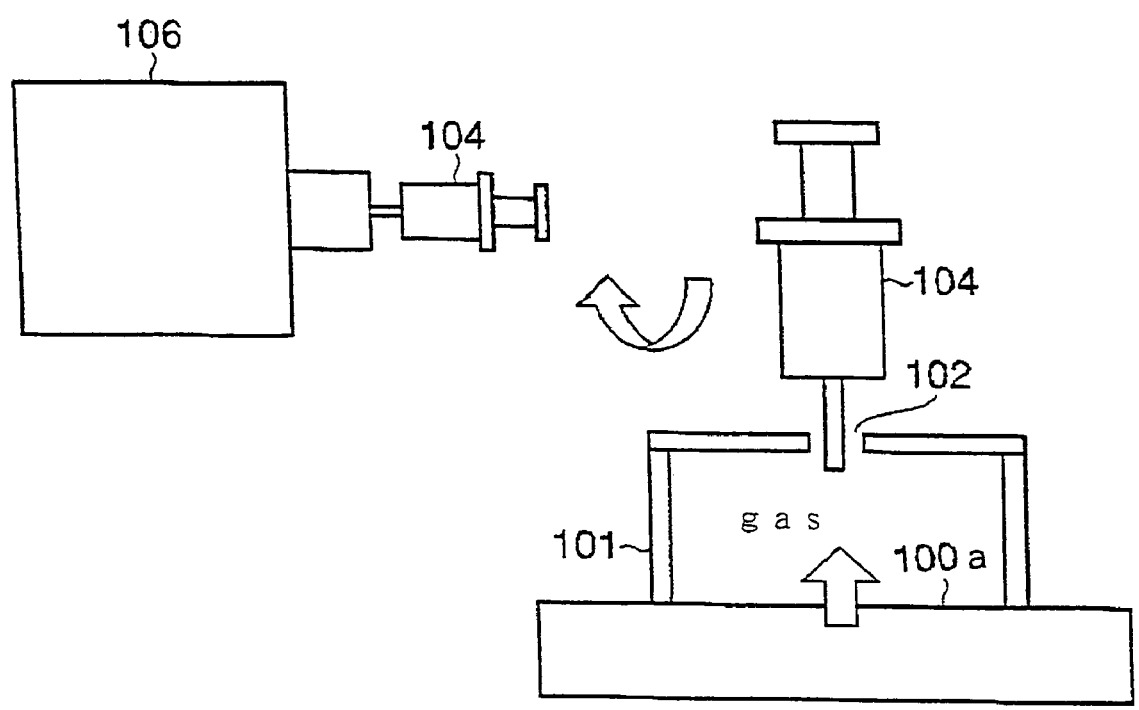
FIG. 15A is a schematic view of a prior art sampling device.
Figure 15B:
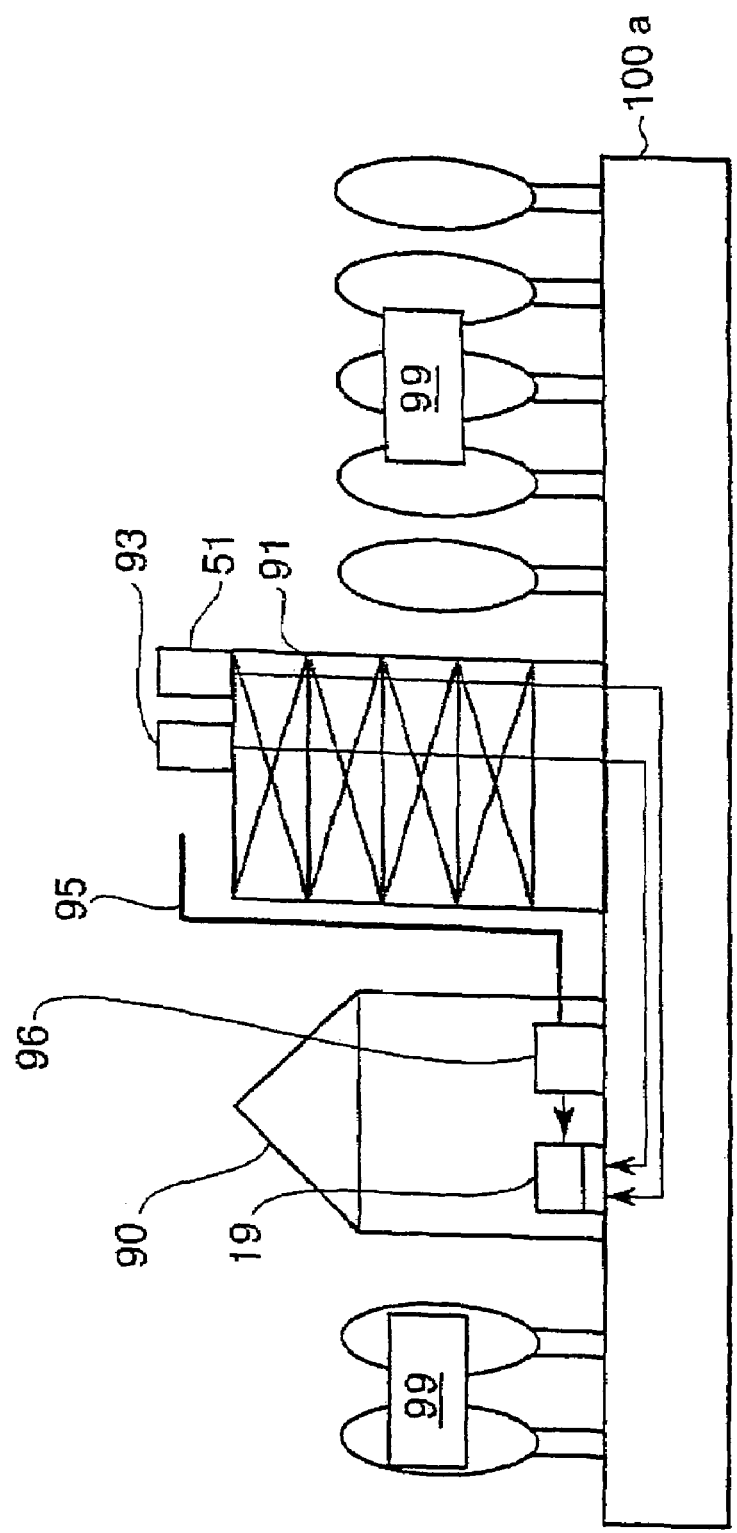
FIG. 15B is a schematic view of a prior art device used for a $CO_2$ absorption quantity measurement in a forest.
Figure 15C:
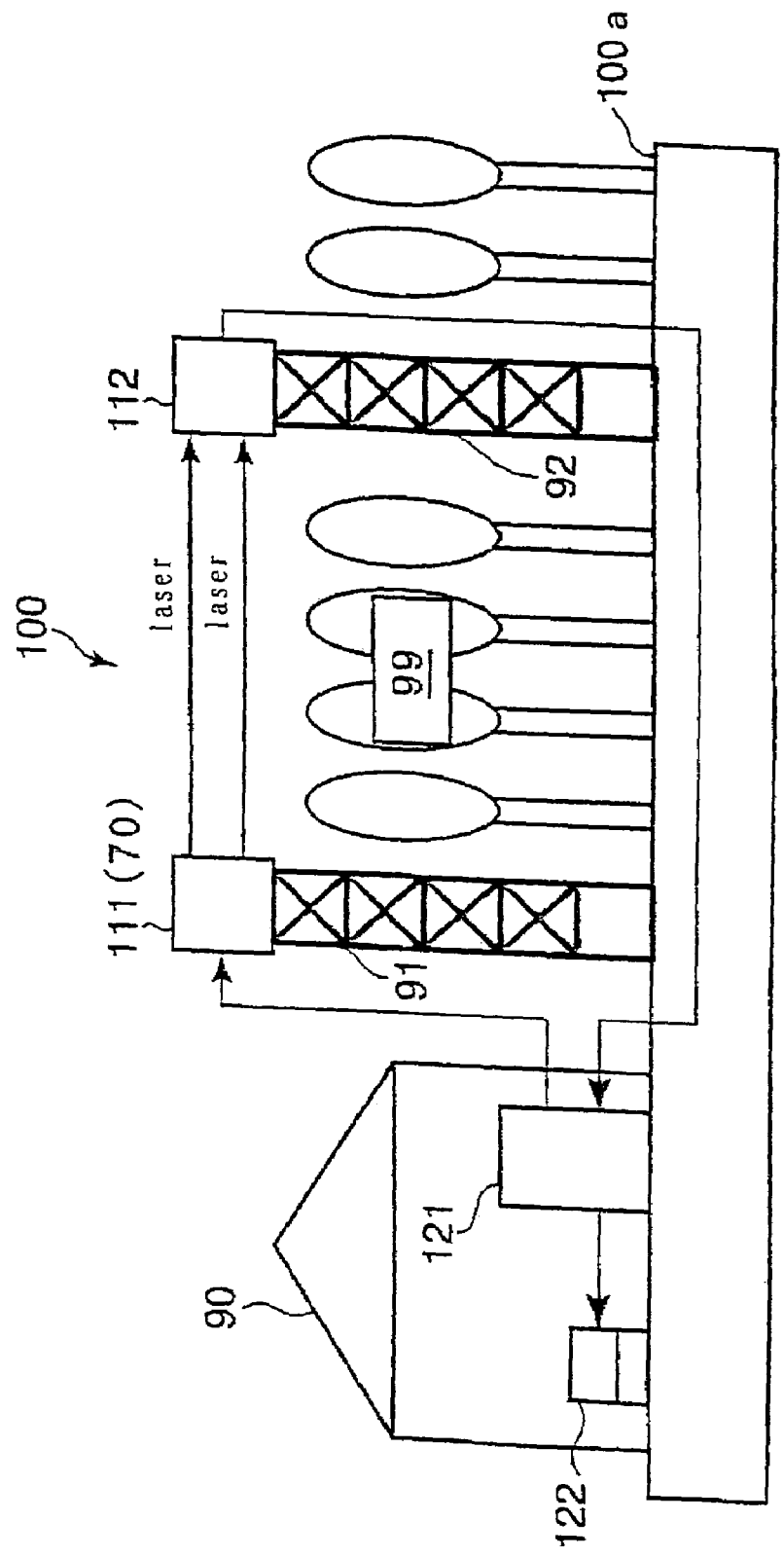
FIG. 15C is a schematic view of a prior art device measuring a momentum flux in a forest according to the scintillation method.
Figure 15D:
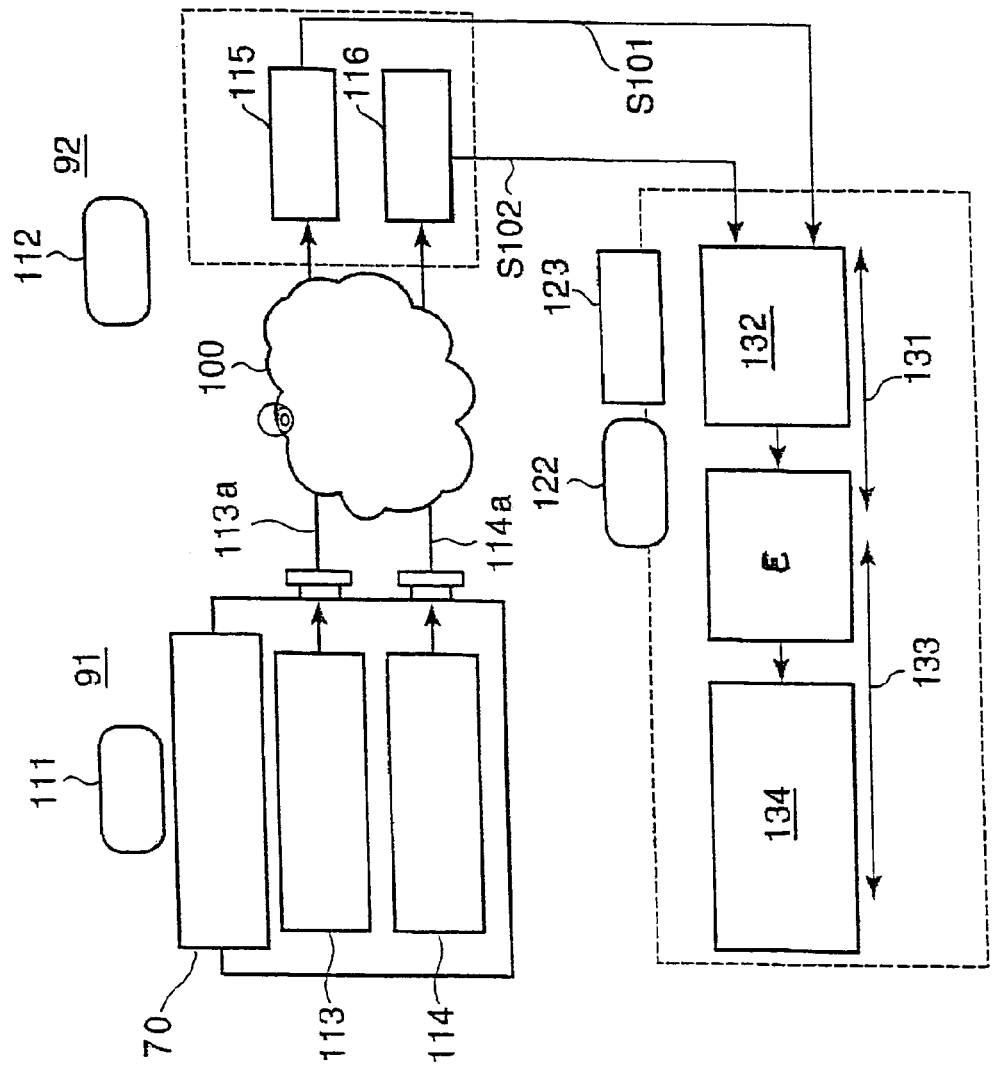
FIG. 15D is a schematic view of a prior art device measuring a momentum flux according to the scintillation method.
Figure 16A:
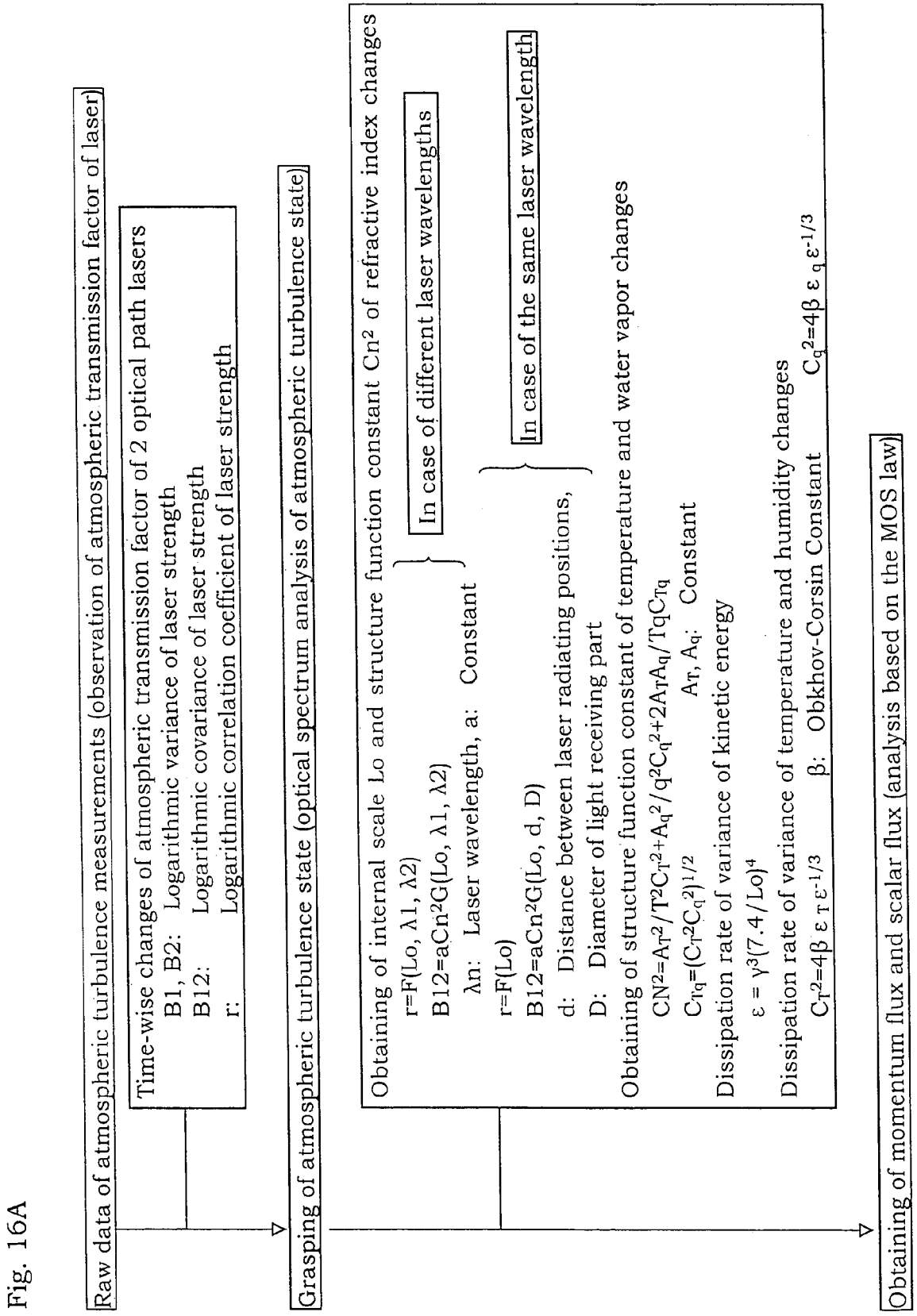
FIG. 16A is a flow chart showing steps for obtaining a momentum flux according to the scintillation method.
Figure 17A:
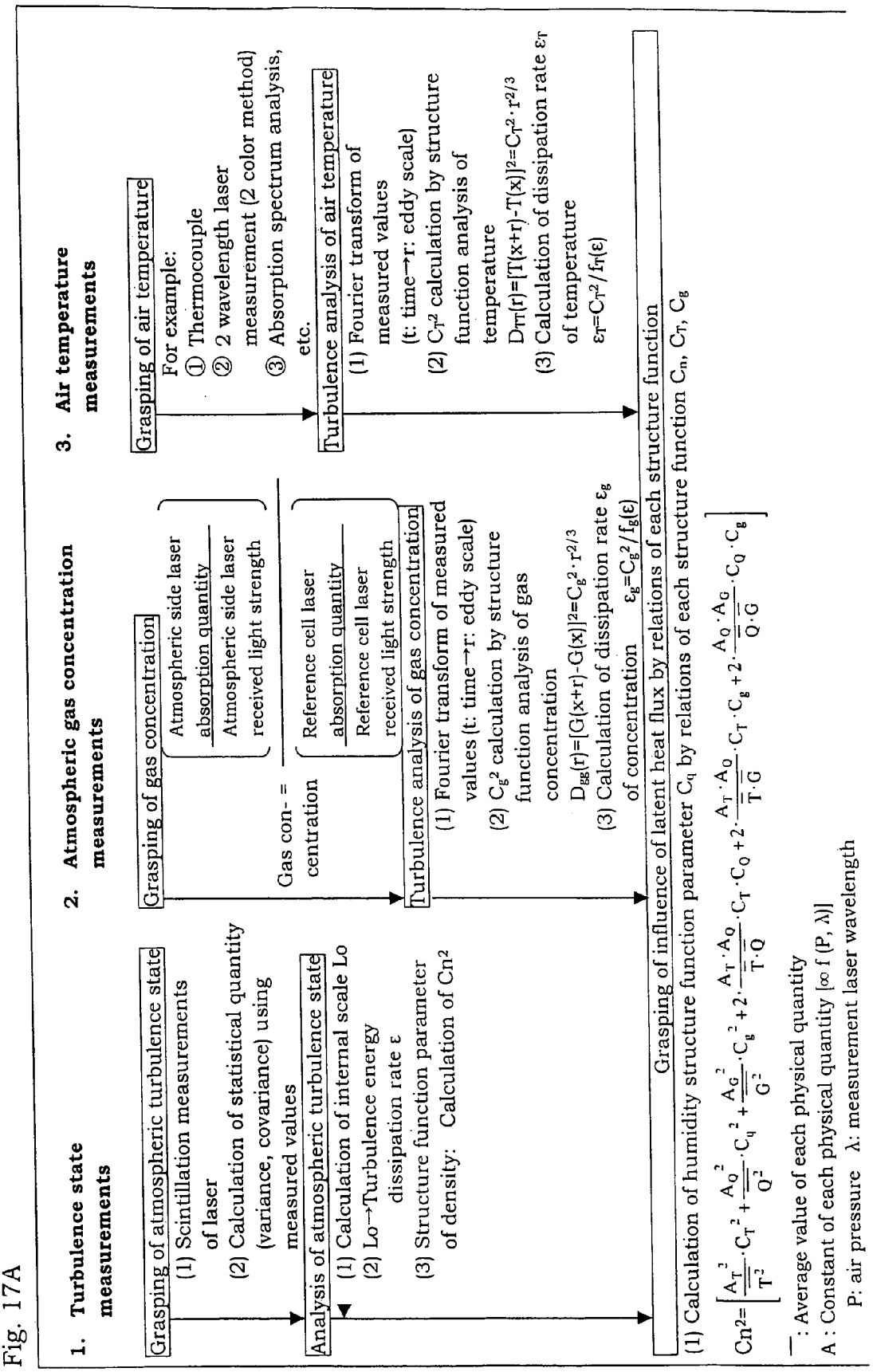
FIG. 17A is a flow chart showing steps for obtaining a gas flux according to the present invention.

Concretely, a light source part 2E provided on a first forest observation tower 91 comprises a TDLAS optical system unit 20 having substantially the same construction as the unit 20 of the above Measurement 1 as well as comprises the scintillation measuring unit 70 shown in FIGS. 15C and D. From the light source part 2E, a reference part received light signal S22 and zero part received light signal S21 as well as a strength modulation reference signal S24 of the scintillation measuring unit 70 are put out into the control/analyzing part 19E of the observation room 90 and, at the same time, an LD control signal S1 is put out from the control/analyzing part 19E of the observation room 90 into the TDLAS optical system unit 20. In the scintillation measuring unit 70, two scintillation measuring laser oscillators 71, 72 are mounted so that an oscillated laser is radiated to the measuring region 100 through optical windows 73a, 73b, respectively, to be received by a light receiving part 3E provided on a second forest observation tower 92.

In the present embodiment, a semi-conductor type pressure sensor 53 and a thermocouple (temperature sensor) 52 are provided on the first forest observation tower 91 and measurement values thereof are representatively used as the pressure and temperature of the measuring region 100. But using characteristics of the absorption spectrum of the measuring object gas, the average pressure and average temperature of the measuring region 100 may also be measured by a laser.

Next, the light receiving part 3E provided on the second forest observation tower 92 comprises a light receiver (PD-G) 35 receiving a laser beam radiated from the TDLAS optical system unit 20 of the light source part 2E provided on the first forest observation tower 91 and transmitted through the atmospheric air and two light receivers (PD-S1, PD-S2) 33, 34 receiving the laser beams radiated from the scintillation measuring unit 70. Respective received light signals S23, S191, S192 (G, S1, S2) thereof are put out into the control/analyzing part 19E of the observation room 90 for analysis.

In the present embodiment, a signal transmission [shown by * mark in FIG. 7(a)] from the light source part 2E and light receiving part 3E on the towers 91, 92 to the observation room 90 is carried out by electric wiring cables using usual metal wires. However, the present invention is not limited thereto but, in order to correspond to cases where the measuring length is further elongated, a signal transmission method by an optical fiber system or wireless system in which communication facilities are easily installed may also be employed.

Figure 8:
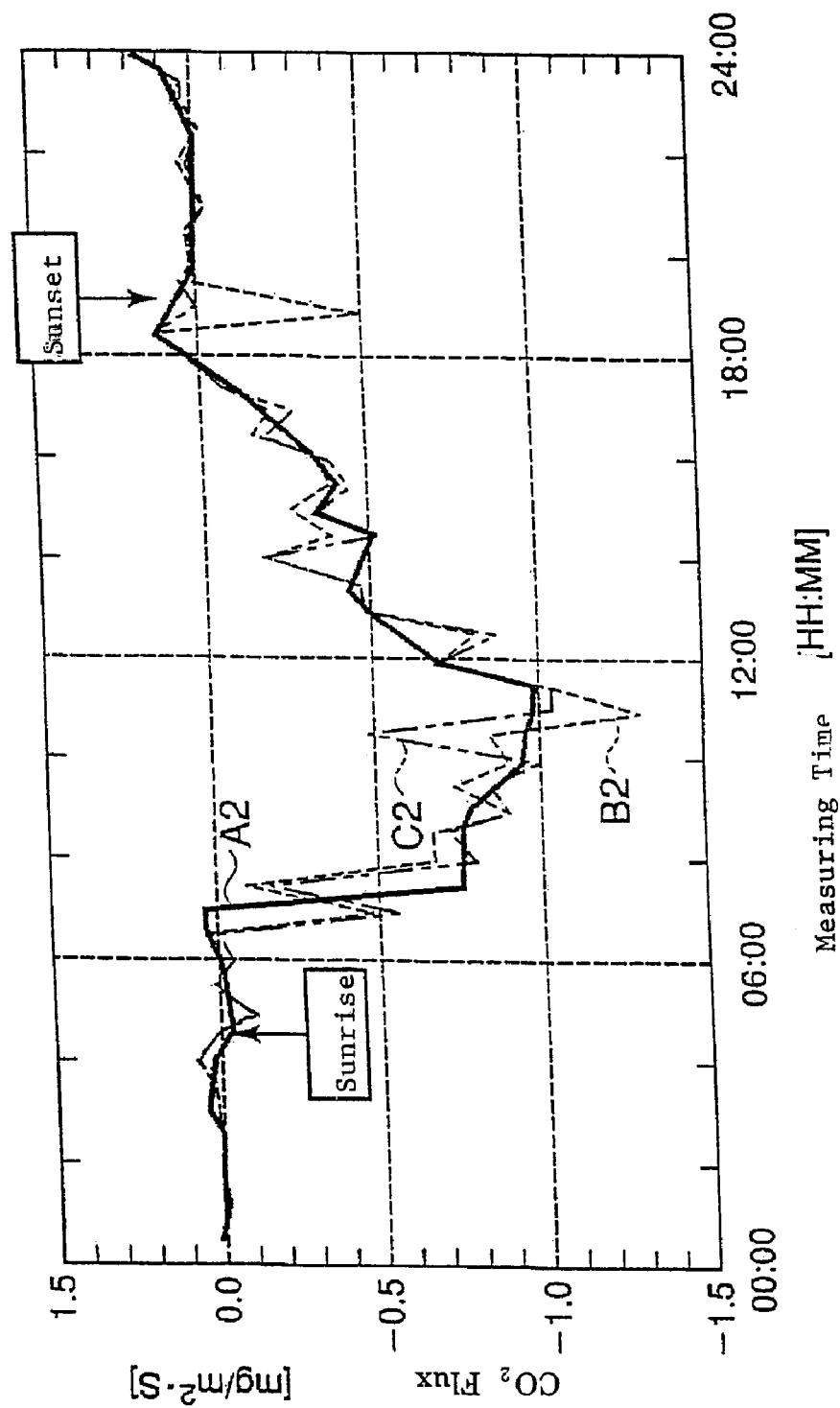
FIG. 8 is a characteristic diagram showing the result of Measurement 2 (measuring the regional $CO_2$ flux between the forest observation towers by the measuring device combined with the scintillation method).

FIG. 8 is a characteristic diagram showing the result of the Measurement 2, wherein the horizontal axis shows the measuring time and the vertical axis shows the measured $CO_2$ flux ($mg/m^2 \cdot S$). There, a solid line A2 shows the result of the Measurement 2 according to the device of the present invention, a broken line B2 shows the result of a comparison example 1 in which the concentration measurement by a prior art $CO_2$ meter and the flux measurement by the ultrasonic current meter on the first observation tower 91 are combined and a two-dot chain line C2 shows the result of a comparison example 2 in which the concentration measurement by a prior art $CO_2$ meter and the flux measurement by an ultrasonic current meter on the second observation tower 92 are combined. As clearly understood from the figure, the result of the present Measurement 2 (the characteristic line A2) forms a change curve that is smoother than the results of the comparison examples 1, 2 (the characteristic lines B2, C2). This is because of the feature of the present invention in that there is no obstruction (or no external disturbance) at all between the light source part and the light receiving part. On the other hand, in the measurement results of the comparison examples using the prior art, there are generated many notches in the change curves. This is because of the prior art problem in that there are provided many measuring devices, creating interferences with each other, in the measuring region and the existence itself of such measuring devices becomes the cause of the external disturbances.

While it is difficult to verify the measurement result of the regional $CO_2$ flux according to the present invention (the characteristic line A2) directly based on the measuring results of the comparison examples using the prior art (the characteristic lines B2, C2), the measurement result of the present invention approximately accords with the result of the measurements carried out on each of the towers using the prior art. Thus, it is verified that the present invention is appropriate for real time measurements of the regional $CO_2$ flux.

Measurement 3

Next, as Measurement 3, an example of measuring the regional $CO_2$ flux between two forest observation towers using a semi-conductor laser type gas flux measuring device according to the present invention as still another embodiment will be described with reference to FIGS. 9(a) and (b). It is to be noted that as to the parts and components of the present embodiment substantially the same as those of the above described embodiments, descriptions thereof will be omitted.

In the present Measurement 3, in order to verify the regional gas flux measurement according to the present invention, a semi-conductor laser type gas flux measuring device system 2F including 3F as a single unit of the wavelength TDLAS type gas concentration measuring device added with a scintillation method function is provided on the forest observation towers 91, 92 and the result of measurements thereof are analyzed based on the MOS law, so that the regional $CO_2$ flux between the forest observation towers 91, 92 is measured. It is to be noted that in the present Measurement 3 also, as in the Measurement 2, the measuring length L2 is set to 81 m, which equals the distance between the towers 91, 92.

FIGS. 9(a) and (b) show a device system used for the present Measurement 3. While the construction of a wavelength TDLAS type gas concentration measuring device system 2F including 3F is substantially the same as the representative device construction shown in FIG. 2, like in the Measurements 1, 2, in order to enhance the measuring sensitivity and measuring stability, a double wavelength modulation mechanism and zero point measuring mechanism are additionally provided. Also, a control/analyzing part 19F provided in the observation room 90 is substantially the same as the control/analyzing part 19D of the Measurement 2 shown in FIGS. 7(a) and (b).

Concretely, a light source part 2F provided on the first forest observation tower 91 is constructed such that the basic construction of the TDLAS optical system unit 20 of the Measurements 1, 2 is provided with a laser oscillator (LD2) 28b separately from a light source (LD1) 28a for gas concentration measuring purpose. From the light source part 2F, a reference part received light signal S22 and zero part received light signal S21 are put out into the control/analyzing part 19F of the observation room 90 and, at the same time, control signals S1a, S1b are put out from the control/analyzing part 19F of the observation room 90 into the respective devices 28a, 28b of the light source part 2F. Also, in the present embodiment, the semi-conductor type pressure sensor 53 and the thermocouple (temperature sensor) 52 are provided on the first forest observation tower 91 and measurement values thereof are representatively used as the pressure and temperature of the measuring region 100.

But using characteristics of the absorption spectrum of the measuring object gas, the average pressure and average temperature of the measuring region 100 may also be measured by a laser.

Next, the light receiving part 3F provided on the second forest observation tower 92 comprises light receivers (PD-G, PD-S) 29a, 29b receiving a laser beam radiated from the optical unit 20 and transmitted through the air between the two towers 91, 92. Respective received light signals S20, S23 thereof are put out into the control/analyzing part 19F of the observation room 90 for analysis. It is to be noted that while in the present embodiment, a signal transmission [shown by * mark in FIG. 9(a)] thereof is carried out by usual electric wiring cables, in order to correspond to cases where the measuring length is further elongated, a signal transmission method by an optical fiber system or wireless system in which communication facilities are easily installed may also be employed.

Figure 10:
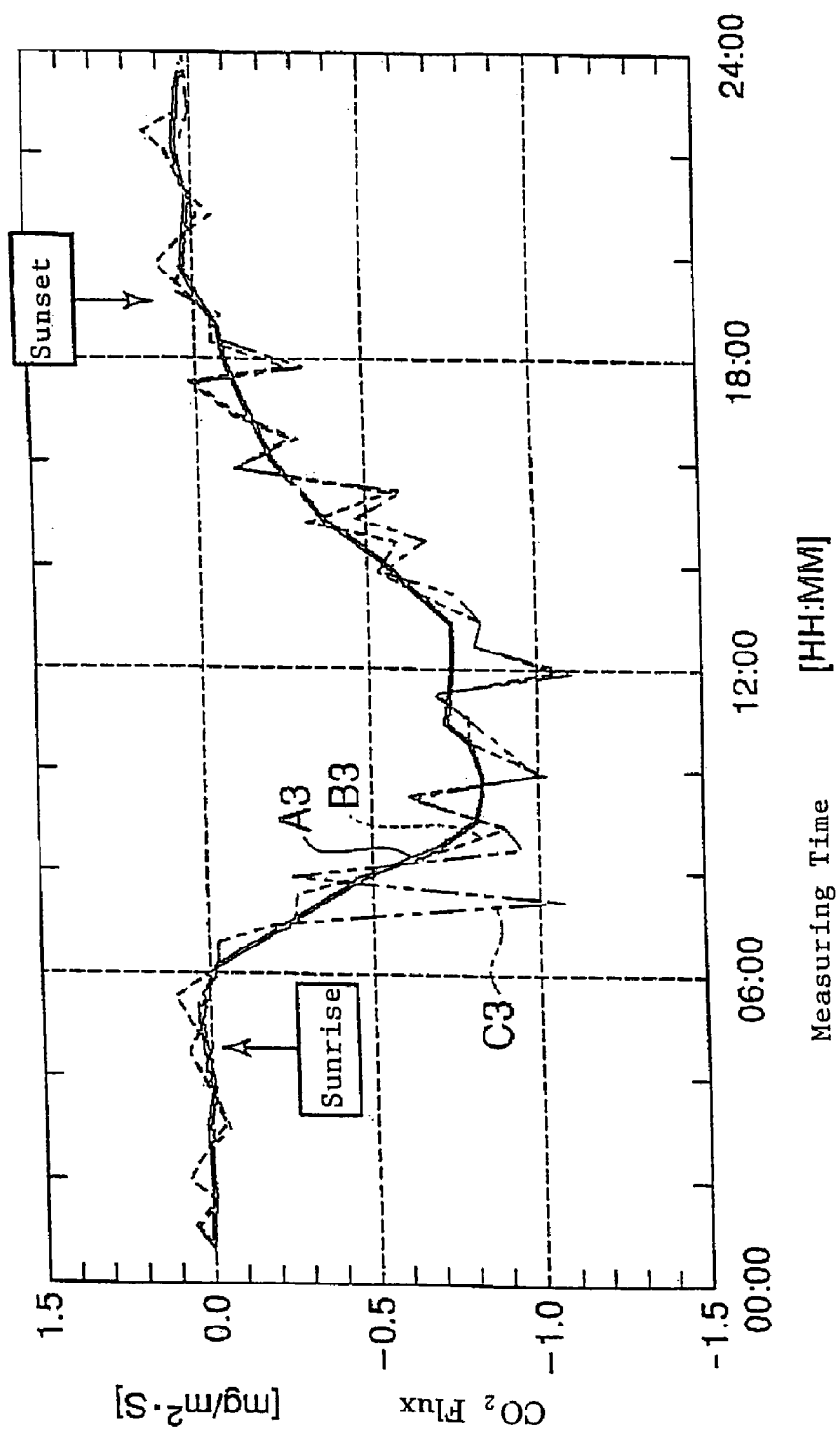
FIG. 10 is a characteristic diagram showing the result of Measurement 3 (measuring the regional $CO_2$ flux between the forest observation towers by a semi-conductor laser type gas flux measuring device).

FIG. 10 is a characteristic diagram showing the result of the Measurement 3, wherein the horizontal axis shows the measuring time and the vertical axis shows the measured $CO_2$ flux (mg/m$^2$·S). There, a solid line A3 shows the result of the Measurement 3 according to the device of the present invention, a broken line B3 shows the result of a comparison example 1 in which the concentration measurement by a prior art $CO_2$ meter and the flux measurement by an ultrasonic current meter on the first observation tower 91 are combined and a two-dot chain line C3 shows the result of a comparison example 2 in which the concentration measurement by a prior art $CO_2$ meter and the flux measurement by an ultrasonic current meter on the second observation tower 92 are combined. As clearly understood from the figure, the result of the present Measurement 3 (the characteristic line A3) forms a change curve that is smoother than the results of the comparison examples 1, 2 (the characteristic lines B3, C3). This is because of the feature of the present invention in that there is no obstruction (or no external disturbance) at all between the light source part and the light receiving part. On the other hand, in the measurement results of the comparison examples using the prior art, there are generated many notches in the change curves. This is because of the prior art problem in that there are provided many measuring devices, creating interferences with each other, in the measuring region and the existence itself of such measurement devices becomes the cause of the external disturbances.

While it is difficult to verify the measurement result of the regional $CO_2$ flux according to the present invention (the characteristic line A3) directly based on the measurement results of the comparison examples using the prior art (the characteristic lines B3, C3), the measurement result of the present invention approximately accords with the result of the measurements carried out on each of the towers using the prior art. Thus, it is verified that the present invention is appropriate for real time measurements of the regional $CO_2$ flux.

Measurement 4

Next, as Measurement 4, an example of measuring the regional $CO_2$ flux between two forest observation towers using a semi-conductor laser type gas flux measuring device according to the present invention as still another embodiment will be described with reference to FIGS. 11(a) and (b). It is to be noted that as to the parts and components of the present embodiment substantially the same as those of the above described embodiments, descriptions thereof will be omitted.

In the present Measurement 4, in order to verify the regional gas flux measurement according to the present invention, a semi-conductor laser type gas flux measuring device system 2G including 3G as a single unit of the wavelength TDLAS type gas concentration measuring device added with a scintillation method function is provided on the forest observation towers 91, 92 and the result of measurements thereof are analyzed based on the MOS law, so that the regional $CO_2$ flux between the forest observation towers 91, 92 is measured. It is to be noted that in the present Measurement 4 also, like in the above-mentioned Measurement 2, the measuring length L2 is set to 81 m that equals the distance between the towers 91, 92.

FIGS. 11(a) and (b) show a device system used for the present Measurement 4. While the construction of the wavelength TDLAS type gas concentration measuring device system is substantially the same as the representative device construction shown in FIG. 3, as in the Measurements 1, 2, in order to enhance the measuring sensitivity and measuring stability, a double wavelength modulation mechanism and zero point measuring mechanism are additionally provided.

Concretely, a light source part 2G provided on the first forest observation tower 91 is constructed such that the basic construction of the TDLAS optical system unit of the Measurements 1, 2 is provided with a polarization plane rotating device 27G distributing a laser beam for measuring purpose to two portions and, while rotating a laser polarization plane of one of the two portions by an angle of 90°, oscillating the laser beam toward the measuring region. Thereby, the reference part received light signal S22 and zero part received light signal S21 are put out into a control/analyzing part 19G of the observation room 90 and, at the same time, the LD control signal S1 is put out from the control/analyzing part 19G of the observation room 90 into the TDLAS optical system unit 20. The polarization plane rotating device 27G comprises a Faraday rotator, so that the polarization plane of the laser beam oscillated from the semi-conductor laser beam source (LD) 28 is rotated and the laser polarization plane is converted between the vertical polarization and the horizontal polarization.

In the present embodiment, the semi-conductor type pressure sensor 53 and the thermocouple (temperature sensor) 52 are provided on the first forest observation tower 91 and measurement values thereof are representatively used as the pressure and temperature of the measuring region 100. But using characteristics of the absorption spectrum of the measuring object gas, the average pressure and average temperature of the measuring region 100 may also be measured by a laser.

Next, the light receiving part 3G provided on the second forest observation tower 92 comprises the two light receivers (PD-G, PD-S) 29a, 29b receiving the two laser beams radiated from the optical unit 20 and transmitted through the air between the two towers 91, 92. The respective received light signals S20, S23 thereof are put out into the control/analyzing part 19G of the observation room 90 for analysis. It is to be noted that while in the present embodiment, a signal transmission [shown by * mark in FIG. 11(a)] thereof is carried out by usual electric wiring cables, in order to correspond to cases where the measuring length is further elongated, a signal transmission method by an optical fiber system or wireless system in which communication facilities are easily installed may also be employed. Further, the control/analyzing part 19G provided in the observation room 90 is substantially the same as that of the Measurement 2 shown in FIGS. 7(a) and (b).

Figure 12:
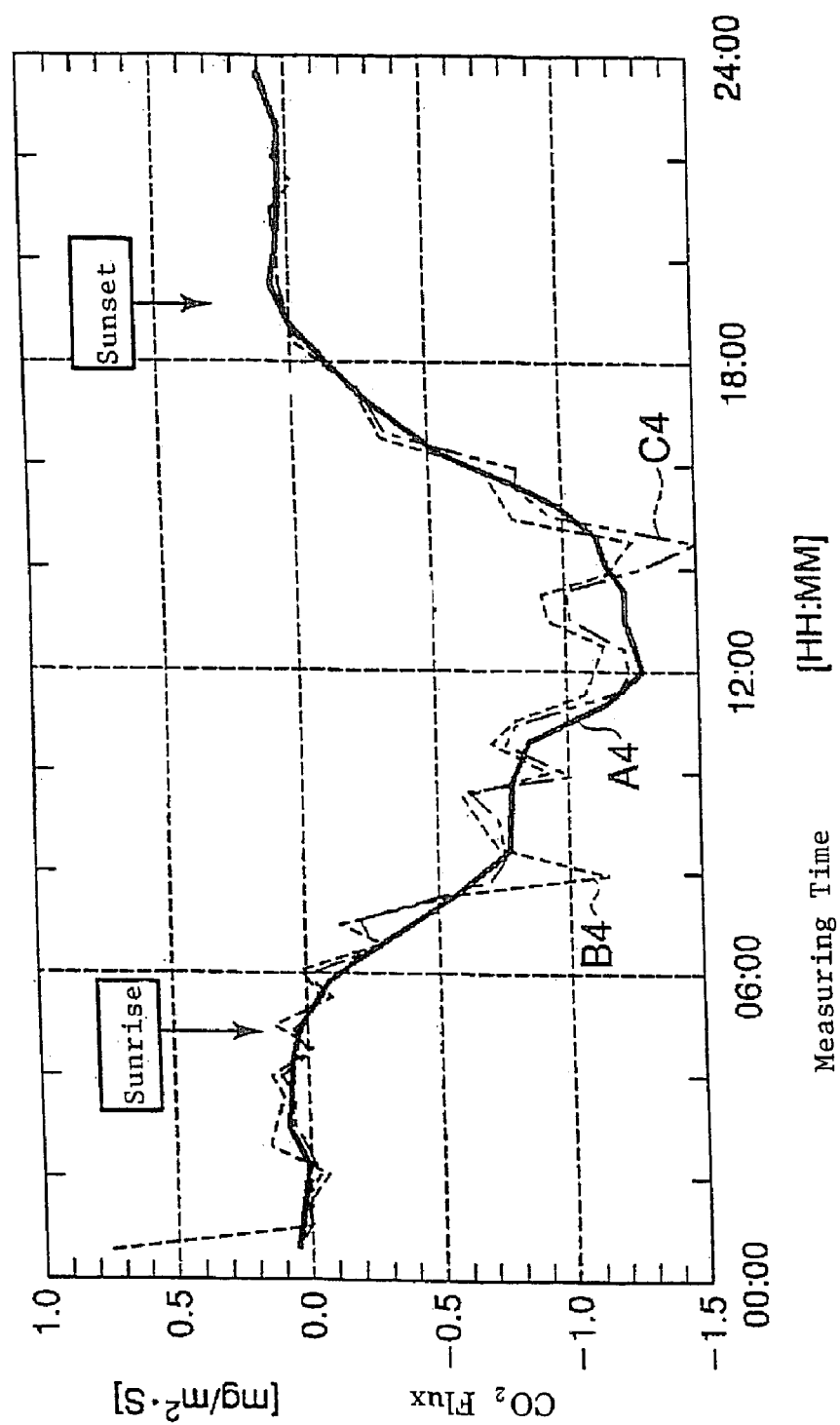
FIG. 12 is a characteristic diagram showing the result of Measurement 4 (measuring the regional $CO_2$ flux between the forest observation towers by a semi-conductor laser type gas flux measuring device).

FIG. 12 is a characteristic diagram showing the result of the Measurement 4, wherein the horizontal axis shows the measuring time and the vertical axis shows the measured $CO_2$ flux ($mg/m^2 \cdot S$). There, a solid line A4 shows the result of the Measurement 4 according to the device of the present invention, a broken line B4 shows the result of a comparison example 1 in which the concentration measurement by a prior art $CO_2$ meter and the flux measurement by an ultrasonic current meter on the first observation tower 91 are combined and a two-dot chain line C4 shows the result of a comparison example 2 in which the concentration measurement by a prior art $CO_2$ meter and the flux measurement by an ultrasonic current meter on the second observation tower 92 are combined.

While it is difficult to verify the measurement result of the regional $CO_2$ flux according to the present invention directly based on the measuring results using the prior art, the measurement result of the present invention approximately accords with the result of the measurements carried out on each of the towers using the prior art. Thus, it is verified that the present invention is appropriate for real time measurements of the regional $CO_2$ flux.

Measurement 5

Next, as Measurement 5, an example of measuring the regional $CO_2$ flux between two forest observation towers using a semi-conductor laser type gas flux measuring device according to the present invention as still another embodiment will be described with reference to FIGS. 13(a) and (b). It is to be noted that as to the parts and components of the present embodiment substantially the same as those of the above described embodiments, descriptions thereof will be omitted.

In the present Measurement 5, in order to verify the regional gas flux measurement according to the present invention, a semi-conductor laser type gas flux measuring device system 2H including 3H as a single unit of the wavelength TDLAS type gas concentration measuring device added with a scintillation method function is provided on the forest observation towers 91, 92 and the result of measurements thereof are analyzed based on the MOS law, so that the regional $CO_2$ flux between the forest observation towers 91, 92 is measured. It is to be noted that in the present Measurement 5 also, as in the above-mentioned Measurement 2, the measuring length L2 is set to 81 m, which equals the distance between the towers 91, 92.

FIGS. 13(a) and (b) show a device system used for the present Measurement 5. As the polarization plane modulation frequency is sufficiently lower as compared with the wavelength modulation frequency, while the construction of the wavelength TDLAS type gas concentration measuring device system is substantially the same as the representative device construction shown in FIG. 4, as in the Measurements 1, 2, in order to enhance the measuring sensitivity and measuring stability, a double wavelength modulation mechanism and zero point measuring mechanism are additionally provided.

Concretely, a light source part 2H provided on the first forest observation tower 91 is constructed such that the basic construction of the TDLAS optical system unit of the Measurements 1, 2 is provided with a polarization plane modulator 59 providing a polarization plane modulating function and the optical unit 20 added with a modulation controller 58 therefor. Thereby, the reference part received light signal S22 and zero part received light signal S21 as well as a polarization plane modulation reference signal S37 are put out into a control/analyzing part 19H of the observation room 90 and, at the same time, the LD control signal S1 is put out from the control/analyzing part 19H of the observation room 90 into the optical system unit 20. In the present embodiment, the semi-conductor type pressure sensor 53 and the thermocouple (temperature sensor) 52 are provided on the first forest observation tower 91 and measurement values thereof are representatively used as the pressure and temperature of the measuring region 100. But using characteristics of the absorption spectrum of the measuring object gas, the average pressure and average temperature of the measuring region 100 may also be measured by a laser.

As compared with the control/analyzing part 19E of the Measurement 2 shown in FIG. 7(a), the control/analyzing part 19H provided in the observation room 90 is additionally provided with a third phase sensitive detector (No. 3-PSD-G) 64e detecting, based on the polarization modulation reference signal S37, a signal component synchronized with the modulation out of the signal put out from the second phase sensitive detector (No. 2-PSD-G) 64a, a phase sensitive detector (No. 1-PD-S) 64f taking out a received light strength signal of the vertically polarized laser or horizontally polarized laser out of the PD-G received light signal and a phase shifter 68 putting out a signal S36 for shifting the phase of the polarization plane modulation reference signal S37 and, instead thereof, the direct current component detector for the received light strength signal is omitted.

The light receiving part 3H provided on the second forest observation tower 92 comprises a light receiver (PD-G) 29 receiving a laser beam radiated from the optical unit 20 and transmitted through the air between the two towers 91, 92. A received light signal S22 thereof is put out into the control/analyzing part 19H of the observation room 90 for analysis. It is to be noted that while in the present embodiment, a signal transmission [shown by * mark in FIG. 13(a)] thereof is carried out by usual electric wiring cables, in order to correspond to cases where the measuring length is further elongated, a signal transmission method by an optical fiber system or wireless system in which communication facilities are easily installed may also be employed.

Figure 14:
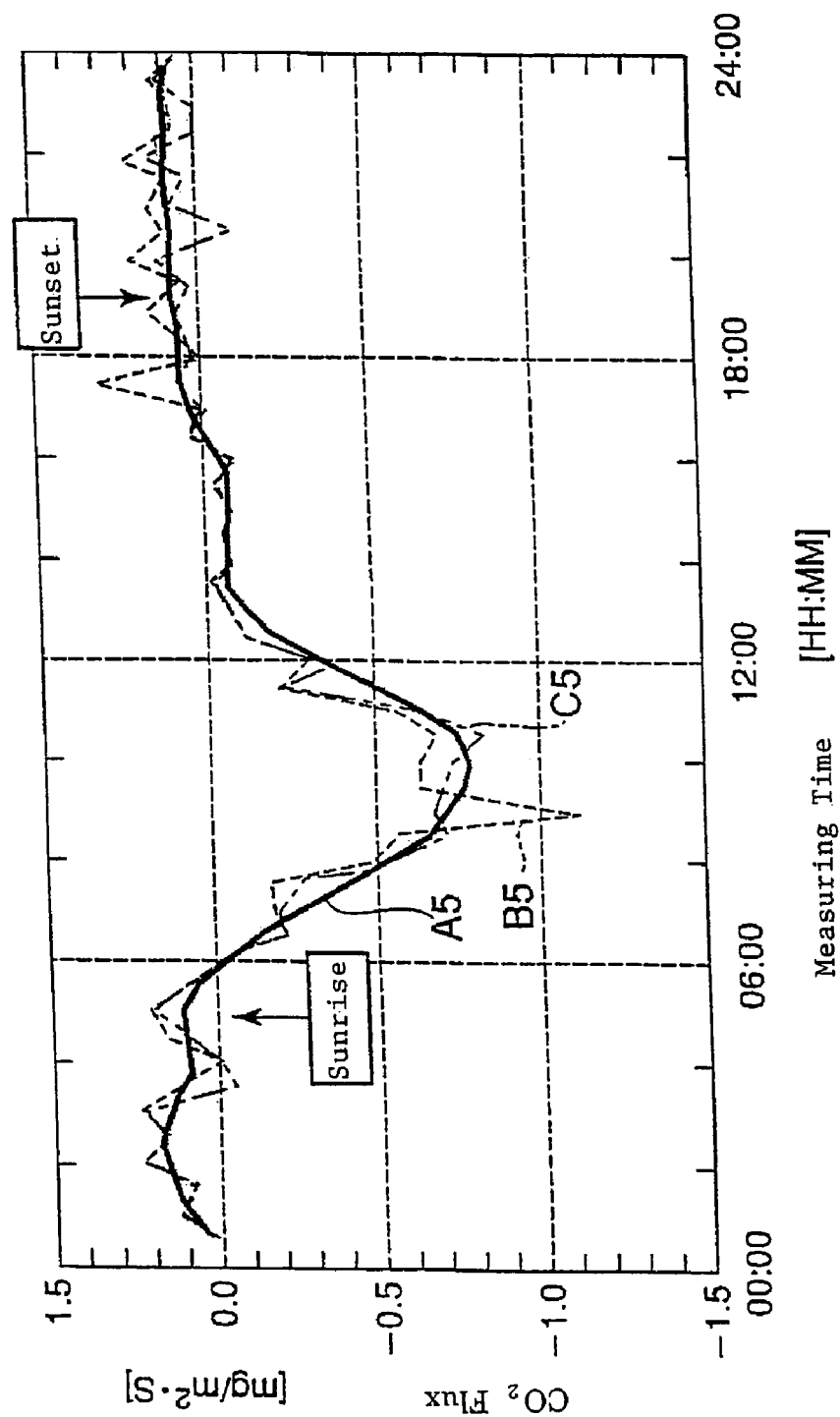
FIG. 14 is a characteristic diagram showing the result of Measurement 5 (measuring the regional $CO_2$ flux by a semi-conductor laser type gas flux measuring device).

FIG. 14 is a characteristic diagram showing the result of the Measurement 5, wherein the horizontal axis shows the measuring time and the vertical axis shows the measured $CO_2$ flux (mg/m²·S). There, a solid line A5 shows the result of the Measurement 5 according to the device of the present invention, a broken line B5 shows the result of a comparison example 1 in which the concentration measurement by a prior art $CO_2$ meter and the flux measurement by an ultrasonic current meter on the first observation tower 91 are combined and a two-dot chain line C5 shows the result of a comparison example 2 in which the concentration measurement by a prior art $CO_2$ meter and the flux measurement by an ultrasonic current meter on the second observation tower 92 are combined.

While it is difficult to verify the measurement result of the regional $CO_2$ flux according to the present invention directly based on the measuring results of the comparison examples using the prior art, the measurement result of the present invention approximately accords with the result of the measurements carried out on each of the towers using the prior art. Thus, it is verified that the present invention is appropriate for real time measurements of the regional $CO_2$ flux.

INDUSTRIAL APPLICABILITY

The gas flux measuring device according to the present invention is appropriate to be used for monitoring an existing quantity of regional greenhouse gases (GHG), that is, for example, for assessing a $CO_2$ absorption quantity by a forest, carrying out an environment investigation, such as an investigation of generation quantity of GHG coming out of the ground, or for detecting a gas leakage of $CO_2$ from underground disposal plants, gas storage facilities, pipelines, etc.

What is claimed is:

1. A gas flux measuring device, wherein said gas flux measuring device comprises:

at least one light source oscillating a laser beam of an absorption wavelength natural to a measuring object gas toward a measuring region, a laser output controller controlling an output action of said light source, a wavelength modulation controller putting out a modulation signal for adding a modulation to an oscillation wavelength of the laser beam oscillated from said light source as well as putting out a reference signal synchronized with the modulation, a first light receiver receiving the laser beam transmitted through the measuring region and putting out a signal corresponding to a received light strength thereof, a first direct current component detector removing an alternating current component as a modulation signal out of the signal put out from said first light receiver and putting out a direct current component of the received light strength, a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region, an optical system distributing the laser beam oscillated from said light source to two or more portions, a reference cell enclosing the measuring object gas of known concentration and being arranged at such a position that the laser beam, distributed by said optical system so as not to be directed to the measuring region, is transmitted through the enclosed gas, a second light receiver receiving the laser beam transmitted through the enclosed gas in said reference cell and putting out a signal corresponding to a received light strength thereof, a second direct current component detector removing an alternating current component as a modulation signal out of the signal put out from said second light receiver and putting out a direct current component of the received light strength, a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell, a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas, an analyzer calculating, based on the signals put out from said first direct current component detector, first wavelength modulation demodulator, second direct current component detector and second wavelength modulation demodulator, the gas concentration and a solid particle concentration in the measuring region and putting out a calculation result thereof, an adder adding the modulation signal from said wavelength modulation controller to the laser wavelength fixing signal from said third wavelength modulation demodulator and putting out an addition signal thereof as an external control signal into said laser output controller, a temperature measuring means measuring a temperature in the measuring region and putting out a signal corresponding to a measured value thereof into said analyzer, a pressure measuring means measuring a pressure in the measuring region and putting out a signal corresponding to a measured value thereof into said analyzer, and a flow velocity measuring means for directly measuring horizontal 2-directional flow velocity components and a vertical flow velocity component of a gas flow in the measuring region and putting out measurement signals thereof into said analyzer, wherein said analyzer carries out an analysis based on the eddy correlation method using the signals inputted from said flow velocity measuring means and, by calculation using an analysis result thereof, obtains a momentum flux in the measuring region, a concentration flux of the measuring object gas and the concentration of the measuring object gas.

2. A gas flux measuring device as claimed in claim 1, wherein said light source and first light receiver are mounted in the same container.

3. A gas flux measuring device as claimed in claim 2, wherein said temperature measuring means and pressure measuring means are also mounted in said same container.

4. A gas flux measuring device as claimed in claim 2, wherein said flow velocity measuring means is an ultrasonic current meter.

5. A gas flux measuring device, wherein
said gas flux measuring device comprises:
at least one first light source oscillating a laser beam of an absorption wavelength natural to a measuring object gas toward a measuring region,
a laser output controller controlling an output action of said first light source,
a wavelength modulation controller putting out a modulation signal for adding a modulation to an oscillation wavelength of the laser beam oscillated from said first light source as well as putting out a reference signal synchronized with the modulation,
a first light receiver receiving the laser beam transmitted through the measuring region and putting out a signal corresponding to a received light strength thereof,
a first direct current component detector removing an alternating current component as a modulation signal out of the signal put out from said first light receiver and putting out a direct current component of the received light strength,
a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region,
an optical system distributing the laser beam oscillated from said first light source to two or more portions,
a reference cell enclosing the measuring object gas of known concentration and being arranged at such a position that the laser beam, distributed by said optical system so as not to be directed to the measuring region, is transmitted through the enclosed gas,
a second light receiver receiving the laser beam transmitted through the enclosed gas in said reference cell and putting out a signal corresponding to a received light strength thereof,
a second direct current component detector removing an alternating current component as a modulation signal out of the signal put out from said second light receiver and putting out a direct current component of the received light strength,
a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell,
a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas,
an analyzer calculating, based on the signals put out from said first direct current component detector, first wavelength modulation demodulator, second direct current component detector and second wavelength modulation demodulator, the gas concentration and a solid particle concentration in the measuring region and putting out a calculation result thereof,
an adder adding the modulation signal from said wavelength modulation controller to the laser wavelength fixing signal from said third wavelength modulation demodulator and putting out an addition signal thereof as an external control signal into said laser output controller,
a temperature measuring means measuring a temperature in the measuring region and putting out a signal corresponding to a measured value thereof into said analyzer,
a pressure measuring means measuring a pressure in the measuring region and putting out a signal corresponding to a measured value thereof into said analyzer, and
a second light source radiating a laser beam to the measuring region and a third light receiver receiving the laser beam radiated from said second light source and transmitted through the measuring region and putting out a signal corresponding to a received light strength thereof into said analyzer;
wherein said analyzer obtains, based on the signal inputted from said third light receiver, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

6. A gas flux measuring device as claimed in claim 5, wherein said light source and first light receiver are mounted in the same container.

7. A gas flux measuring device as claimed in claim 6, wherein said temperature measuring means and pressure measuring means are also mounted in said same container.

8. A gas flux measuring device, wherein
said gas flux measuring device comprises:
a first light source oscillating a laser beam of an absorption wavelength natural to a measuring object gas toward a measuring region,
a laser output controller controlling an output action of said first light source,
a wavelength modulation controller putting out a modulation signal for adding a modulation to an oscillation wavelength of the laser beam oscillated from said first light source as well as putting out a reference signal synchronized with the modulation,
a first light receiver receiving the laser beam transmitted through the measuring region and putting out a signal corresponding to a received light strength thereof,
a first direct current component detector removing an alternating current component as a modulation signal out of the signal put out from said first light receiver and putting out a direct current component of the received light strength,
a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region,
an optical system distributing the laser beam oscillated from said first light source to two or more portions,
a reference cell enclosing the measuring object gas of known concentration and being arranged at such a position that the laser beam, distributed by said optical system so as not to be directed to the measuring regions is transmitted through the enclosed gas,
a second light receiver receiving the laser beam transmitted through the enclosed gas in said reference cell and putting out a signal corresponding to a received light strength thereof,
a second direct current component detector removing an alternating current component as a modulation signal out of the signal put out from said second light receiver and putting out a direct current component of the received light strength,
a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell,
a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas,
an analyzer calculating, based on the signals put out from said first direct current component detector, first wavelength modulation demodulator, second direct current component detector and second wavelength modulation demodulator, the gas concentration and a solid particle concentration in the measuring region and putting out a calculation result thereof,
an adder adding the modulation signal from said wavelength modulation controller to the laser wavelength fixing signal from said third wavelength modulation demodulator and putting out an addition signal thereof as an external control signal into said laser output controller,
a temperature measuring means measuring a temperature in the measuring region and putting out a signal corresponding to a measured value thereof into said analyzer,
a pressure measuring means measuring a pressure in the measuring region and putting out a signal corresponding to a measured value thereof into said analyzer,
a second light source oscillating a laser beam of the absorption wavelength natural to the measuring object gas toward the measuring region,
a third light receiver receiving the laser beam oscillated from said second light source and transmitted through the measuring region and putting out a signal corresponding to a received light strength thereof, and
a third direct current component detector removing an alternating current component as a modulation signal out of the signal received from said third light receiver and putting out a direct current component of the received light strength into said analyzer;
wherein said analyzer obtains, based on the signal inputted from said third direct current component detector, time-wise changes of a laser transmission factor, obtains, based on these time-wise changes of the laser transmission factor, time-wise changes of a gas density, carries out an analysis based on the Monin-Obukhov similarity law in order to grasp a turbulence state of the measuring object gas using the time-wise changes of the gas density and obtains, by calculation using an analysis result thereof, a momentum flux in the measuring region, a concentration flux of the measuring object gas and the concentration of the measuring object gas.

9. A gas flux measuring device as claimed in claim 8, wherein said light source and first light receiver are mounted in the same container.

10. A gas flux measuring device as claimed in claim 9, wherein said temperature measuring means and pressure measuring means are also mounted in said same container.

11. A gas flux measuring device, wherein
said gas flux measuring device, comprises:
a single light source oscillating a laser beam of an absorption wavelength natural to a measuring object gas toward a measuring region,
a laser output controller controlling an output action of said light source,
a wavelength modulation controller putting out a modulation signal for adding a modulation to an oscillation wavelength of the laser beam oscillated from said light source as well as putting out a reference signal synchronized with the modulation, a first light receiver receiving the laser beam transmitted through the measuring region and putting out a signal corresponding to a received light strength thereof, a first direct current component detector removing an alternating current component as a modulation signal out of the signal put out from said first light receiver and putting out a direct current component of the received light strength, a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region, an optical system distributing the laser beam oscillated from said light source to two or more portions, a reference cell enclosing the measuring object gas of known concentration and being arranged at such a position that the laser beam, distributed by said optical system so as not to be directed to the measuring regions is transmitted through the enclosed gas, a second light receiver receiving the laser beam transmitted through the enclosed gas in said reference cell and putting out a signal corresponding to a received light strength thereof, a second direct current component detector removing an alternating current component as a modulation signal out of the signal put out from said second light receiver and putting out a direct current component of the received light strength, a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell, a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas, an analyzer calculating, based on the signals put out from said first direct current component detector, first wavelength modulation demodulator, second direct current component detector and second wavelength modulation demodulator, the gas concentration and a solid particle concentration in the measuring region and putting out a calculation result thereof, an adder adding the modulation signal from said wavelength modulation controller to the laser wavelength fixing signal from said third wavelength modulation demodulator and putting out an addition signal thereof as an external control signal into said laser output controller, a temperature measuring means measuring a temperature in the measuring region and putting out a signal corresponding to a measured value thereof into said analyzer, a pressure measuring means measuring a pressure in the measuring region and putting out a signal corresponding to a measured value thereof into said analyzer, a polarization plane rotating device having said optical system distributing the laser beam oscillated from said single light source to two or more portions and rotating a polarization plane of the laser beam of the two or more portions distributed by said optical system, a third light receiver receiving the laser beam of which polarization plane is rotated by said polarization plane rotating device and putting out a signal corresponding to a received light strength thereof, and a third direct current component detector removing an alternating current component as a modulation signal out of the signal received from said third light receiver and putting out a direct current component of the received light strength into said analyzer;

wherein said analyzer obtains, based on the signal inputted from said third direct current component detector, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

12. A gas flux measuring device as claimed in claim 11, wherein said light source and first light receiver are mounted in the same container.

13. A gas flux measuring device as claimed in claim 12, wherein said temperature measuring means and pressure measuring means are also mounted in said same container.

14. A gas flux measuring device, wherein
said gas flux measuring device comprises:

a single light source oscillating a laser beam of an absorption wavelength natural to a measuring object gas toward a measuring region, a laser output controller controlling an output action of said light source, a wavelength modulation controller putting out a modulation signal for adding a modulation to an oscillation wavelength of the laser beam oscillated from said light source as well as putting out a reference signal synchronized with the modulation, a first light receiver receiving the laser beam transmitted through the measuring region and putting out a signal corresponding to a received light strength thereof, a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region, an optical system distributing the laser beam oscillated from said light source to two or more portions, a reference cell enclosing the measuring object gas of known concentration and being arranged at such a position that the laser beam distributed by said optical system so as not to be directed to the measuring region is transmitted through the enclosed gas, a second light receiver receiving the laser beam transmitted through the enclosed gas in said reference cell and putting out a signal corresponding to a received light strength thereof, a direct current component detector removing an alternating current component as a modulation signal out of the signal put out from said second light receiver and putting out a direct current component of the received light strength, a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell, a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas, an analyzer calculating, based on the signals put out from said first wavelength modulation demodulator, said direct current component detector and said second wavelength modulation demodulator, the gas concentration and a solid particle concentration in the measuring region and putting out a calculation result thereof, an adder adding the modulation signal from said wavelength modulation controller to the laser wavelength fixing signal from said third wavelength modulation demodulator and putting out an addition signal thereof as an external control signal into said laser output controller, a temperature measuring means measuring a temperature in the measuring region and putting out a signal corresponding to a measured value thereof into said analyzer, a pressure measuring means measuring a pressure in the measuring region and putting out a signal corresponding to a measured value thereof into said analyzer, a polarization plane rotating device having a Faraday rotator externally controlled and rotating a polarization plane of the laser beam oscillated from said single light source, a polarization plane modulation controller controlling a rotation angle of said Faraday rotator so as to change over the laser polarization plane between a vertical polarization and a horizontal polarization with a predetermined period, a first polarization plane demodulator detecting, based on a strength modulation reference signal from said polarization plane modulation controller, a signal synchronized with a polarization plane modulation out of the signal put out from said first light receiver and putting out a signal in proportion to a received light strength of a vertically polarized laser beam transmitted through the measuring region as a measuring region laser absorption quantity signal into said analyzer, a second polarization plane demodulator detecting, based on the strength of the modulation reference signal from said polarization plane modulation controller, a signal synchronized with the polarization plane modulation out of the signal put out from said first light receiver and putting out a signal in proportion to a received light strength of a horizontally polarized laser beam transmitted through the measuring region as a measuring region laser absorption quantity signal into said analyzer, and a third polarization plane demodulator detecting, based on the strength modulation reference signal from said polarization plane modulation controller, a signal synchronized with the polarization plane modulation out of the signal put out from said first light receiver and putting out a signal in proportion to a received light strength of the laser beam transmitted through the measuring region as a concentration measurement signal into said analyzer;

wherein said analyzer obtains, based on the signals inputted from said first, second and third polarization plane demodulators, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

15. A gas flux measuring device as claimed in claim 14, wherein said third polarization plane demodulator is provided downstream of said first wavelength modulation demodulator and a polarization plane modulation frequency thereof is set lower than a wavelength modulation frequency thereof.

16. A gas flux measuring device as claimed in claim 14, wherein said third polarization plane demodulator is provided upstream of said first wavelength modulation demodulator and a polarization plane modulation frequency thereof is set higher than a wavelength modulation frequency thereof.

17. A gas flux measuring device as claimed in claim 14, further comprising a signal phase converter provided upstream of said first and second polarization plane demodulators for converting a phase of the polarization plane modulation reference signal from said polarization plane modulation controller.

18. A gas flux measuring device as claimed in claim 14, wherein said light source and first light receiver are mounted in the same container.

19. A gas flux measuring device as claimed in claim 18, wherein said temperature measuring means and pressure measuring means are also mounted in said same container.

20. A gas flux measuring device, wherein said gas flux measuring device comprises:

a first light source oscillating a laser beam of an absorption wavelength natural to a measuring object gas toward a measuring region, a laser output controller controlling an output action of said first light source, a wavelength modulation controller putting out a modulation signal for adding a modulation to an oscillation wavelength of the laser beam oscillated from said first light source as well as putting out a reference signal synchronized with the modulation, a first light receiver receiving the laser beam transmitted through the measuring region and putting out a signal corresponding to a received light strength thereof, a first direct current component detector removing an alternating current component as a modulation signal out of the signal put out from said first light receiver and putting out a direct current component of the received light strength, a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region, an optical system distributing the laser beam oscillated from said first light source to two or more portions, a reference cell enclosing the measuring object gas of known concentration and being arranged at such a position that the laser beam, distributed by said optical system so as not to be directed to the measuring region, is transmitted through the enclosed gas, a second light receiver receiving the laser beam transmitted through the enclosed gas in said reference cell and putting out a signal corresponding to a received light strength thereof, a second direct current component detector removing an alternating current component as a modulation signal out of the signal put out from said second light receiver and putting out a direct current component of the received light strength, a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell, a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas, an analyzer calculating, based on the signals put out from said first direct current component detector, first wavelength modulation demodulator, second direct current component detector and second wavelength modulation demodulator, the gas concentration and a solid particle concentration in the measuring region and putting out a calculation result thereof, an adder adding the modulation signal from said wavelength modulation controller to the laser wavelength fixing signal from said third wavelength modulation demodulator and putting out an addition signal thereof as an external control signal into said laser output controller, a temperature measuring means measuring a temperature in the measuring region and putting out a signal corresponding to a measured value thereof into said analyzer, a pressure measuring means measuring a pressure in the measuring region and putting out a signal corresponding to a measured value thereof into said analyzer, a second light source oscillating a laser beam of the absorption wavelength natural to the measuring object gas toward the measuring region, a third light receiver receiving the laser beam oscillated from said second light source and transmitted through the measuring region and putting out a signal corresponding to a received light strength thereof, and a polarization plane modulation demodulator detecting a signal synchronized with polarization plane modulation out of the signal put out from said first light receiver and putting out a signal in proportion to a received light strength thereof, wherein said analyzer obtains, based on a signal inputted from said polarization plane modulation demodulator, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

21. A gas flux measuring device, wherein said gas flux measuring device comprises:

a single light source oscillating a laser beam of an absorption wavelength natural to a measuring object gas toward a measuring region, a laser output controller controlling an output action of said light source, a wavelength modulation controller putting out a modulation signal for adding a modulation to an oscillation wavelength of the laser beam oscillated from said light source as well as putting out a reference signal synchronized with the modulation, a first light receiver receiving the laser beam transmitted through the measuring region and putting out a signal corresponding to a received light strength thereof, a first direct current component detector removing an alternating current component as a modulation signal out of the signal put out from said first light receiver and putting out a direct current component of the received light strength, a first wavelength modulation demodulator detecting, based on the reference signal from said wavelength modulation controller, an even number order harmonic component of the wavelength modulation signal added to the laser beam out of the signal put out from said first light receiver and putting out a signal in proportion to a concentration of the measuring object gas in the measuring region, an optical system distributing the laser beam oscillated from said light source to two or more portions, a reference cell enclosing the measuring object gas of known concentration and being arranged at such a position that the laser beam, distributed by said optical system so as not to be directed to the measuring region, is transmitted through the enclosed gas, a second light receiver receiving the laser beam transmitted through the enclosed gas in said reference cell and putting out a signal corresponding to a received light strength thereof, a second direct current component detector removing an alternating current component as a modulation signal out of the signal put out from said second light receiver and putting out a direct current component of the received light strength, a second wavelength modulation demodulator detecting, based on the reference signal from said wavelength modulation controller, an even number order harmonic component of the wavelength modulation signal added to the laser beam out of the signal put out from said second light receiver and putting out a signal in proportion to the concentration of the enclosed gas in said reference cell, a third wavelength modulation demodulator detecting, based on the reference signal from said wavelength modulation controller, an odd number order harmonic component of the wavelength modulation signal added to the laser beam out of the signal put out from said second light receiver and putting out a laser wavelength fixing signal as a standard signal for fixing the laser beam wavelength to the absorption wavelength of the measuring object gas, an analyzer calculating, based on the signals put out from said first direct current component detector, first wavelength modulation demodulator, second direct current component detector and second wavelength modulation demodulator, the gas concentration and a solid particle concentration in the measuring region and putting out a calculation result thereof, an adder adding the modulation signal from said wavelength modulation controller to the laser wavelength fixing signal from said third wavelength modulation demodulator and putting out an addition signal thereof as an external control signal into said laser output controller, a temperature measuring means measuring a temperature in the measuring region and putting out a signal corresponding to a measured value thereof into said analyzer, a pressure measuring means measuring a pressure in the measuring region and putting out a signal corresponding to a measured value thereof into said analyzer, a polarization plane rotating device having the optical system distributing the laser beam oscillated from said single light source to two or more portions and rotating a polarization plane of the laser beam of the one or more portions distributed by said optical system, a third light receiver receiving the laser beam of which polarization plane is rotated by said polarization plane rotating device and putting out a signal corresponding to a received light strength thereof, and a polarization plane modulation demodulator detecting a signal synchronized with the polarization plane modulation out of the signal put out from said first light receiver and putting out a signal in proportion to a received light strength thereof;

said analyzer obtains, based on the signal inputted from said polarization plane modulation demodulator, time-wise changes of a laser transmission factor, obtains, based on these time-wise changes of the laser transmission factor, time-wise changes of a gas density, carries out an analysis based on the Monin-Obukhov similarity law in order to determine a turbulence state of the measuring object gas using the time-wise changes of the gas density and obtains, by calculation using an analysis result thereof, a momentum flux in the measuring region, a concentration flux of the measuring object gas and the concentration of the measuring object gas.

* * * * *